US010413584B1

(12) United States Patent
Jaynes et al.

(10) Patent No.: US 10,413,584 B1
(45) Date of Patent: Sep. 17, 2019

(54) PEPTIDES HAVING IMMUNOMODULATORY PROPERTIES

(71) Applicant: Riptide Bioscience, Inc., Vallejo, CA (US)

(72) Inventors: Jesse Jaynes, Auburn, AL (US); Henry Wilfred Lopez, Napa, CA (US); George R. Martin, Rockville, MD (US); Clayton Yates, Auburn, AL (US); Charles Garvin, Redwood City, CA (US)

(73) Assignee: Riptide Bioscience, Inc., Vallejo, CA (US)

( * ) Notice: Subject to any disclaimer, the term of this patent is extended or adjusted under 35 U.S.C. 154(b) by 0 days.

(21) Appl. No.: 16/116,619

(22) Filed: Aug. 29, 2018

(51) Int. Cl.
*A61K 38/08* (2019.01)
*A61P 35/00* (2006.01)
*A61P 29/00* (2006.01)

(52) U.S. Cl.
CPC .............. *A61K 38/08* (2013.01); *A61P 29/00* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 5,717,064 | A | 2/1998 | Julian et al. |
| 5,861,478 | A | 1/1999 | Jaynes |
| 5,962,410 | A | 10/1999 | Jaynes |
| 6,255,282 | B1 | 7/2001 | Jaynes |
| 6,514,581 | B1 | 2/2003 | Jaynes |
| 6,559,281 | B1 | 5/2003 | Jaynes |
| 6,635,740 | B1 | 10/2003 | Enright |
| 7,566,777 | B2 | 7/2009 | Enright |
| 8,258,100 | B2 | 9/2012 | Enright |
| 8,569,230 | B2 | 10/2013 | Yount et al. |
| 8,734,775 | B2 | 5/2014 | Yates-Binder |
| 9,090,655 | B2 | 7/2015 | Cheng et al. |
| 9,492,499 | B2 | 11/2016 | Jaynes |
| 10,016,480 | B2 | 7/2018 | Rudloff |
| 10,017,542 | B2 | 7/2018 | Jaynes |
| 2002/0155132 | A1 | 10/2002 | Jaynes |
| 2004/0018967 | A1 | 1/2004 | Enright |
| 2005/0187151 | A1 | 8/2005 | Strom |
| 2008/0153748 | A1 | 6/2008 | Jaynes |
| 2010/0016227 | A1 | 1/2010 | Enright |
| 2012/0270770 | A1 | 10/2012 | Jaynes |
| 2014/0128312 | A1 | 5/2014 | Jaynes et al. |
| 2014/0329753 | A1 | 11/2014 | Jaynes |
| 2016/0296594 | A1 | 10/2016 | Jaynes et al. |
| 2017/0020956 | A1 | 1/2017 | Jaynes |

FOREIGN PATENT DOCUMENTS

| | | |
|---|---|---|
| WO | WO90/12866 | 11/1990 |
| WO | WO93/03749 | 3/1993 |
| WO | WO95/28832 | 11/1995 |
| WO | WO96/03519 | 2/1996 |
| WO | WO96/03522 | 2/1996 |
| WO | WO98/42634 | 10/1998 |
| WO | WO00/73433 | 12/2000 |
| WO | WO2004/033715 | 4/2004 |
| WO | WO2005/046714 | 5/2005 |
| WO | WO-2006100096 A2 * | 9/2006 ............. C07K 14/78 |
| WO | WO2012/050892 | 4/2012 |

OTHER PUBLICATIONS

U.S. Appl. No. 15/286,491, filed Oct. 5, 2016, Jaynes.
U.S. Appl. No. 16/000,709, filed Jun. 5, 2018, Jaynes.
U.S. Appl. No. 16/165,727, filed Oct. 19, 2018, Jaynes.
Partial Supplementary European Search Report from European Application No. EP15851584, dated May 30, 2018, 17 pages.
Blondell, S. et al. "Optimization and High-Throughput Screening of Antimicrobial Peptides," Current Pharmaceutical Design, vol. 16, No. 28, Sep. 1, 2010, pp. 3204-3211.
Clemens, Edward L. et al. "Designed Host Defense Peptides for the Treatment of Bacterial Keratitis", Investigative Ophthalmology & Visual Science, vol. 58, No. 14, Dec. 14, 2017, p. 6273.
Jankowski et al. "Anti-inflammatory effect of oxytocin in rat myocardial infarction," Basic Res Cardiol., (2010) 105(2):205-18.
Jaynes et al. "Structure/Function Link Between Cytokine Domains and Natural and Designed Lytic Peptides: Medical Promise," (2012) American Chemical Society, pp. 21-45.

(Continued)

*Primary Examiner* — Vanessa L. Ford
*Assistant Examiner* — Sandra E Dillahunt
(74) *Attorney, Agent, or Firm* — Bret E. Field; Bozicevic, Field & Francis LLP

(57) ABSTRACT

The present disclosure provides novel peptides that having immunomodulatory activities in vitro and in vivo. The peptides can include a particular striapathic region of alternating hydrophilic and hydrophobic modules that can adopt an amphipathic conformation under physiological conditions. This disclosure provides peptides that can specifically bind to key functional regions on one or more signaling proteins, particularly pro-inflammatory cytokines, macrophage inhibition proteins, and histone regulation proteins. This disclosure includes peptides that are sufficiently stable in the circulation to allow for intravenous administration. Pharmaceutical compositions including the subject peptides are also provided. The subject peptides find use in methods of modulating macrophage activity. In some cases, the peptide is a CD206-binding agent. Also provided are methods of treating a subject for a condition associated with chronic inflammation using the peptides and compositions of this disclosure.

19 Claims, 4 Drawing Sheets
Specification includes a Sequence Listing.

(56) References Cited

OTHER PUBLICATIONS

Ko et al. "FOLFIRINOX: A Small Step or a Great Leap Forward?" Journal of Clinical Oncology, vol. 29 No. 28, Oct. 1, 2011, pp. 3727-3729.

OXYTOCIN, NCBI, PRF:229114, GI:229114 (Jul. 10, 1992), 1 page, also available at http://www.ncbi.nlm.nig.gov/protein/229114 (last visited Jan. 28, 2016).

Park et al. "Melittin Inhibits Inflammatory Target Gene Expression and Mediator Generation Via Interaction With kappaB Kinase," Biochemical Pharmacology, Sep. 29, 2006, vol. 73, No. 2, pp. 237-247.

Raventos, D. et al. "Improving on Nature's Defenses: Optimization & High Throughput Screening of Antimicrobial Peptides," Current Topics in Medicinal Chemistry, Bentham Science Publishers Ltd, vol. 8, No. 2, May 1, 2005, pp. 219-233.

Smith et al. "Effects of Synthetic Amphiphilic α-Helical Peptides on the Electrochemical and Structural Properties of Supported Hybrid Bilayers on Gold," Langmuir, vol. 22(4):1919-1927 (Jan. 20, 2006).

Wang et al. "A Cell-Penetrating Peptide Suppresses Inflammation by Inhibiting NF-Kappa-Beta Signaling," Molecular Therapy, May 10, 2011, vol. 19, No. 10, pp. 1849-1857.

Water, from http://www.biologyOnline.org/dictionary/Water, pp. 1-3, accessed Apr. 24, 2014.

Muta, et al., "Tachyplesins Isolated from Hemocytes of Southeast Asian Horseshoe Crabs (Carcinoscorpis rotundicauda and Tachypleus gigas): Identification of a New Tachyplesin, Tachyplesin III, and a Processing Intermediate of Its Precursor", J. Biochem.,vol. 108, No. 2,1990, pp. 261-266.

Sawabe, T. et al., Hypothetical Protein JCM19233_786 [Vibrio sp. C7], Genbank entry [online], Oct. 17, 2014 [retrieved on Dec. 14, 2018], <URL: https://www.ncbi.nlm.nih.gov/protein/GAL09809.1>; p. 1.

Panda, et al., Hypothetical Protein KCO_01177 [*Pectobacterium carotovorum* subsp. *brasiliensis* ICMP 19477], Genbank entry [online], Jun. 24, 2015 [retrieved on Dec. 14, 2018], <URL: https://www.ncbi.nlm.nih.gov/protein/KMK85879.1>, pp. 1-2.

* cited by examiner

SEQUENCE LISTING

<160> NUMBER OF SEQ ID NOS: 41

<210> SEQ ID NO 1
<211> LENGTH: 10
<212> TYPE: PRT
<213> ORGANISM: Artificial Sequence
<220> FEATURE:
<223> OTHER INFORMATION: Synthetic sequence

<400> SEQUENCE: 1

Arg Trp Lys Phe Gly Gly Phe Lys Trp Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic sequence

<400> SEQUENCE: 2

Phe Trp Lys Arg Phe Val Arg Lys Trp Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic sequence

<400> SEQUENCE: 3

Phe Lys Trp Arg Gly Gly Arg Trp Lys Phe
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic sequence

<400> SEQUENCE: 4

Phe Trp Lys Arg Gly Gly Arg Lys Trp Phe
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Synthetic sequence

<400> SEQUENCE: 5

Phe Trp Lys Arg Phe Val
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic sequence

<400> SEQUENCE: 6

Phe Val Arg Lys Trp Arg
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic sequence

<400> SEQUENCE: 7

Phe Trp Lys Lys Phe Val Lys Lys Trp Lys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic sequence

<400> SEQUENCE: 8

Gly Asp Arg Gly Ile Lys Gly His Arg Gly Phe
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic sequence

<400> SEQUENCE: 9

Glu Lys Leu Ser Ala Phe Arg Asn Phe Phe
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic sequence

<400> SEQUENCE: 10

Phe Tyr Pro Asp Phe Phe Lys Lys Phe Phe
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic sequence

<400> SEQUENCE: 11

Phe Phe Arg His Phe Ala Thr His Leu Asp
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic sequence

<400> SEQUENCE: 12

Leu Tyr Lys Lys Ile Ile Lys Lys Leu Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic sequence

<400> SEQUENCE: 13

Trp Trp His His Trp Trp His His Trp His
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic sequence

<400> SEQUENCE: 14

Trp Trp Arg His Trp Trp His Arg Trp Arg
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic sequence

<400> SEQUENCE: 15

Trp Trp Lys His Trp Trp His Lys Trp Lys
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic sequence

<400> SEQUENCE: 16

Lys Lys Ile Arg Val Arg Leu Ser Ala
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic sequence

<400> SEQUENCE: 17

Phe Gln Phe Leu Gly Lys Ile Ile His His
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic sequence

<400> SEQUENCE: 18

Phe Phe Arg Lys Ser Lys Glu Lys Ile Gly
1               5                   10

```
<210> SEQ ID NO 19
<211> LENGTH: 5
<212> TYPE: PRT
<213> ORGANISM: Artificial Sequence
<220> FEATURE:
<223> OTHER INFORMATION: Synthetic sequence

<400> SEQUENCE: 19

Phe Ala Phe Ala Phe
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic sequence

<400> SEQUENCE: 20

Lys Phe Arg Lys Ala Phe Lys Arg Phe Phe
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic sequence

<400> SEQUENCE: 21

Phe Phe Arg Lys Phe Ala Lys Arg Phe Lys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic sequence

<400> SEQUENCE: 22

Phe Phe Lys Lys Phe Phe Lys Lys Phe Lys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic sequence

<400> SEQUENCE: 23

Lys Phe Lys Lys Phe Phe Lys Lys Phe Phe
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic sequence

<400> SEQUENCE: 24

Lys Phe Lys Lys Ala Phe Lys Lys Ala Phe
1               5                   10

<210> SEQ ID NO 25
```

```
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (2)..(2)
<223> OTHER INFORMATION: Xaa is a lysine or arginine
<220> FEATURE:
<221> NAME/KEY: Misc_feature
<222> LOCATION: (7)..(7)
<223> OTHER INFORMATION: Xaa is a lysine or arginine
<220> FEATURE:
<221> NAME/KEY: Misc_feature
<222> LOCATION: (9)..(10)
<223> OTHER INFORMATION: Xaa is a alanine or phenylalanine

<400> SEQUENCE: 25

Glu Xaa Leu Ser Ala Phe Xaa Asn Xaa Xaa
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (2)..(2)
<223> OTHER INFORMATION: Xaa is a phenylalanine, tyrosine or leucine
<220> FEATURE:
<221> NAME/KEY: Misc_feature
<222> LOCATION: (9)..(9)
<223> OTHER INFORMATION: Xaa is a phenylalanine, tyrosine or leucine

<400> SEQUENCE: 26

Leu Xaa Lys Lys Ile Ile Lys Lys Xaa Leu
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (5)..(6)
<223> OTHER INFORMATION: Xaa is a phenylalanine or tyrosine
<220> FEATURE:
<221> NAME/KEY: Misc_feature
<222> LOCATION: (7)..(8)
<223> OTHER INFORMATION: Xaa is lysine or arginine
<220> FEATURE:
<221> NAME/KEY: Misc_feature
<222> LOCATION: (9)..(10)
<223> OTHER INFORMATION: Xaa is a phenylalanine or tyrosine

<400> SEQUENCE: 27

Phe Tyr Pro Asp Xaa Xaa Xaa Xaa Xaa Xaa
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(2)
```

```
<223> OTHER INFORMATION: Xaa is a phenylalanine or tyrosine
<220> FEATURE:
<221> NAME/KEY: Misc_feature
<222> LOCATION: (3)..(4)
<223> OTHER INFORMATION: Xaa is a lysine or arginine

<400> SEQUENCE: 28

Xaa Xaa Xaa Xaa Ser Lys Glu Lys Ile Gly
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(2)
<223> OTHER INFORMATION: Xaa is a phenylalanine or alanine
<220> FEATURE:
<221> NAME/KEY: Misc_feature
<222> LOCATION: (3)..(4)
<223> OTHER INFORMATION: Xaa is a Ornithine
<220> FEATURE:
<221> NAME/KEY: Misc_feature
<222> LOCATION: (5)..(6)
<223> OTHER INFORMATION: Xaa is a phenylalanine or alanine
<220> FEATURE:
<221> NAME/KEY: Misc_feature
<222> LOCATION: (7)..(8)
<223> OTHER INFORMATION: Xaa is a Ornithine
<220> FEATURE:
<221> NAME/KEY: Misc_feature
<222> LOCATION: (9)..(9)
<223> OTHER INFORMATION: Xaa is a phenylalanine or alanine
<220> FEATURE:
<221> NAME/KEY: Misc_feature
<222> LOCATION: (10)..(10)
<223> OTHER INFORMATION: Xaa is a Ornithine

<400> SEQUENCE: 29

Xaa Xaa Xaa Xaa Xaa Xaa Xaa Xaa Xaa Xaa
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (3)..(4)
<223> OTHER INFORMATION: Xaa is ornithine, lysine or arginine
<220> FEATURE:
<221> NAME/KEY: Misc_feature
<222> LOCATION: (7)..(8)
<223> OTHER INFORMATION: Xaa is ornithine, lysine or arginine
<220> FEATURE:
<221> NAME/KEY: Misc_feature
<222> LOCATION: (9)..(9)
<223> OTHER INFORMATION: Xaa is phenylalanine or alanine
<220> FEATURE:
<221> NAME/KEY: Misc_feature
<222> LOCATION: (11)..(11)
<223> OTHER INFORMATION: Xaa is ornithine, lysine or arginine

<400> SEQUENCE: 30

Phe Ala Xaa Xaa Phe Ala Xaa Xaa Xaa Phe Xaa
1               5                   10

<210> SEQ ID NO 31
```

```
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (4)..(4)
<223> OTHER INFORMATION: Xaa is lysine or arginine
<220> FEATURE:
<221> NAME/KEY: Misc_feature
<222> LOCATION: (7)..(7)
<223> OTHER INFORMATION: Xaa is lysine or arginine
<220> FEATURE:
<221> NAME/KEY: Misc_feature
<222> LOCATION: (10)..(10)
<223> OTHER INFORMATION: Xaa is lysine or arginine

<400> SEQUENCE: 31

Phe Trp Lys Xaa Phe Val Xaa Lys Trp Xaa
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (3)..(3)
<223> OTHER INFORMATION: Xaa is histidine, lysine or arginine
<220> FEATURE:
<221> NAME/KEY: Misc_feature
<222> LOCATION: (8)..(8)
<223> OTHER INFORMATION: Xaa is histidine, lysine or arginine
<220> FEATURE:
<221> NAME/KEY: Misc_feature
<222> LOCATION: (10)..(10)
<223> OTHER INFORMATION: Xaa is histidine, lysine or arginine

<400> SEQUENCE: 32

Trp Trp Xaa His Trp Trp His Xaa Trp Xaa
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(2)
<223> OTHER INFORMATION: Xaa is phenylalanine or alanine
<220> FEATURE:
<221> NAME/KEY: Misc_feature
<222> LOCATION: (3)..(3)
<223> OTHER INFORMATION: Xaa is lysine or arginine
<220> FEATURE:
<221> NAME/KEY: Misc_feature
<222> LOCATION: (5)..(6)
<223> OTHER INFORMATION: Xaa is phenylalanine or alanine

<400> SEQUENCE: 33

Xaa Xaa Xaa His Xaa Xaa Thr His Leu Asp
1               5                   10

<210> SEQ ID NO 34
<211> LENGTH: 10
<212> TYPE: PRT
<213> ORGANISM: Artificial Sequence
<220> FEATURE:
```

```
<223> OTHER INFORMATION: Synthetic sequence
<220> FEATURE:
<221> NAME/KEY: Misc_feature
<222> LOCATION: (1)..(1)
<223> OTHER INFORMATION: Xaa is phenylalanine, tyrosine or leucine
<220> FEATURE:
<221> NAME/KEY: Misc_feature
<222> LOCATION: (3)..(3)
<223> OTHER INFORMATION: Xaa is phenylalanine, tyrosine or leucine
<220> FEATURE:
<221> NAME/KEY: Misc_feature
<222> LOCATION: (6)..(6)
<223> OTHER INFORMATION: Xaa is lysine or arginine

<400> SEQUENCE: 34

Xaa Gln Xaa Leu Gly Xaa Ile Ile His His
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (2)..(3)
<223> OTHER INFORMATION: Xaa is lysine, arginine, histidine, aspartic
      acid, glutamic acid, asparagine or glutamine
<220> FEATURE:
<221> NAME/KEY: Misc_feature
<222> LOCATION: (5)..(5)
<223> OTHER INFORMATION: Xaa is phenylalanine, tryptophan, alanine,
      isoleucine or valine
<220> FEATURE:
<221> NAME/KEY: Misc_feature
<222> LOCATION: (6)..(6)
<223> OTHER INFORMATION: Xaa is lysine, arginine, histidine, aspartic
      acid, glutamic acid, asparagine or glutamine
<220> FEATURE:
<221> NAME/KEY: Misc_feature
<222> LOCATION: (8)..(9)
<223> OTHER INFORMATION: Xaa is lysine, arginine, histidine, aspartic
      acid, glutamic acid, asparagine or glutamine
<220> FEATURE:
<221> NAME/KEY: Misc_feature
<222> LOCATION: (11)..(11)
<223> OTHER INFORMATION: Xaa is phenylalanine, tryptophan, alanine,
      isoleucine or valine

<400> SEQUENCE: 35

Gly Xaa Xaa Gly Xaa Xaa Gly Xaa Xaa Gly Xaa
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (3)..(3)
<223> OTHER INFORMATION: Xaa is lysine or arginine
<220> FEATURE:
<221> NAME/KEY: Misc_feature
<222> LOCATION: (6)..(6)
<223> OTHER INFORMATION: Xaa is lysine or arginine
<220> FEATURE:
<221> NAME/KEY: Misc_feature
<222> LOCATION: (9)..(9)
<223> OTHER INFORMATION: Xaa is lysine or arginine

<400> SEQUENCE: 36
```

```
Gly Asp Xaa Gly Ile Xaa Gly His Xaa Gly Phe
1               5                   10
```

<210> SEQ ID NO 37
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(2)
<223> OTHER INFORMATION: Xaa is lysine or arginine
<220> FEATURE:
<221> NAME/KEY: Misc_feature
<222> LOCATION: (4)..(4)
<223> OTHER INFORMATION: Xaa is lysine or arginine
<220> FEATURE:
<221> NAME/KEY: Misc_feature
<222> LOCATION: (6)..(6)
<223> OTHER INFORMATION: Xaa is lysine or arginine

<400> SEQUENCE: 37

```
Xaa Xaa Ile Xaa Val Xaa Leu Ser Ala
1               5
```

<210> SEQ ID NO 38
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (3)..(4)
<223> OTHER INFORMATION: Xaa is lysine or arginine
<220> FEATURE:
<221> NAME/KEY: Misc_feature
<222> LOCATION: (6)..(7)
<223> OTHER INFORMATION: Xaa is lysine or arginine

<400> SEQUENCE: 38

```
Phe Trp Xaa Xaa Thr Xaa Xaa Trp Phe
1               5
```

<210> SEQ ID NO 39
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(2)
<223> OTHER INFORMATION: Xaa is tryptophan or phenylalanine
<220> FEATURE:
<221> NAME/KEY: Misc_feature
<222> LOCATION: (8)..(9)
<223> OTHER INFORMATION: Xaa is tryptophan or phenylalanine

<400> SEQUENCE: 39

```
Xaa Xaa Lys Arg Thr Arg Lys Xaa Xaa
1               5
```

<210> SEQ ID NO 40
<211> LENGTH: 4
<212> TYPE: PRT
<213> ORGANISM: Artificial Sequence
<220> FEATURE:
<223> OTHER INFORMATION: Synthetic sequence

<400> SEQUENCE: 40

```
Gly Gly Gly Arg
1

<210> SEQ ID NO 41
<211> LENGTH: 4
<212> TYPE: PRT
<213> ORGANISM: Artificial Sequence
<220> FEATURE:
<223> OTHER INFORMATION: Synthetic sequence

<400> SEQUENCE: 41

Gly Pro Gly Arg
1
```

PEPTIDES HAVING IMMUNOMODULATORY PROPERTIES

INTRODUCTION

Acute inflammation is the initial response of a tissue to harmful stimuli. It involves a complex, highly regulated process that begins when cells present in the injured tissue, including macrophages, dendritic cells, histiocytes, Kupffer cells, and mastocytes, sense molecules associated with the injury and become activated. Upon activation, these cells release inflammatory mediators, such as vasodilators. The vasodilators induce increased blood flow and permeability of the blood vessels in the vicinity of the injury. This, in turn, results in the increased movement of plasma and leukocytes (including neutrophils and macrophages) from the blood into the injured tissue. Because inflammatory mediators are, in general, rapidly degraded, acute inflammation requires constant stimulation in order to be sustained. As a result, acute inflammation ends once the harmful stimulus is removed.

Various agents, including but not limited to bacteria, viruses, physical injury, chemical injury, cancer, chemotherapy, and radiation therapy, can, depending on the specific agent and the genetic makeup of the animal exposed to it, cause prolonged and excessive inflammation. Such inflammation, known as chronic inflammation, is believed to be a contributing factor to many widespread and debilitating diseases, including heart disease, cancer, respiratory disease, stroke, neurological diseases such as Alzheimer's disease, diabetes, and kidney disease. The result of chronic inflammation is the destruction of normal tissue and its replacement with collagen-rich connective tissue. Collagen-rich connective tissue, also known as scar tissue, exhibits diminished tissue function as compared to normal tissue. Persistent and prolonged formation of scar tissue, in turn, leads to fibrosis. Fibrosis is among the common symptoms of diseases affecting the lungs, skin, liver, heart, and bone marrow, and is a critical factor in diseases such as idiopathic pulmonary fibrosis, scleroderma, keloids, liver cirrhosis, myocardial fibrosis, diabetic kidney disease, myelodysplastic syndrome, and other disorders.

Studies of chronic inflammation and fibrosis have indicated that, regardless of the activating agent and the tissue affected, a common network of signaling proteins tend to function together to establish the pro-inflammatory state. This network of signaling proteins includes a number of different cytokines, cytokine receptors, transcription factors, and micro RNAs, including TGFβ, TGFβRII, and miRNA19b. Therapeutic agents that reduce inflammation without harmful side effects are therefore of great interest.

SUMMARY

Novel peptides that have immunomodulatory activities in vitro and in vivo are provided. The peptides can include a particular striapathic region of alternating hydrophilic and hydrophobic modules that can adopt an amphipathic conformation under physiological conditions. The peptides can specifically bind to key functional regions on one or more signaling proteins, particularly pro-inflammatory cytokines, macrophage inhibition proteins, and/or histone regulation proteins. This disclosure includes peptides that are sufficiently stable in the circulation in vivo after administration to a subject. Pharmaceutical compositions including the subject peptides are also provided.

The subject peptides find use in methods of modulating macrophage activity. In some cases, the peptide is a CD206-binding agent. Also provided are methods of treating a subject for a condition associated with chronic inflammation using the peptides and compositions of this disclosure.

These and other features and advantages of the compositions and methods of the invention will be set forth or will become more fully apparent in the description that follows and in the appended claims. For example, suitable immunomodulatory polypeptides may be identified by use of the formula and sequences described herein. Furthermore, features and advantages of the described compositions and methods may be learned by practicing the methods or will be obvious from the description.

DETAILED DESCRIPTION

Figure 1:
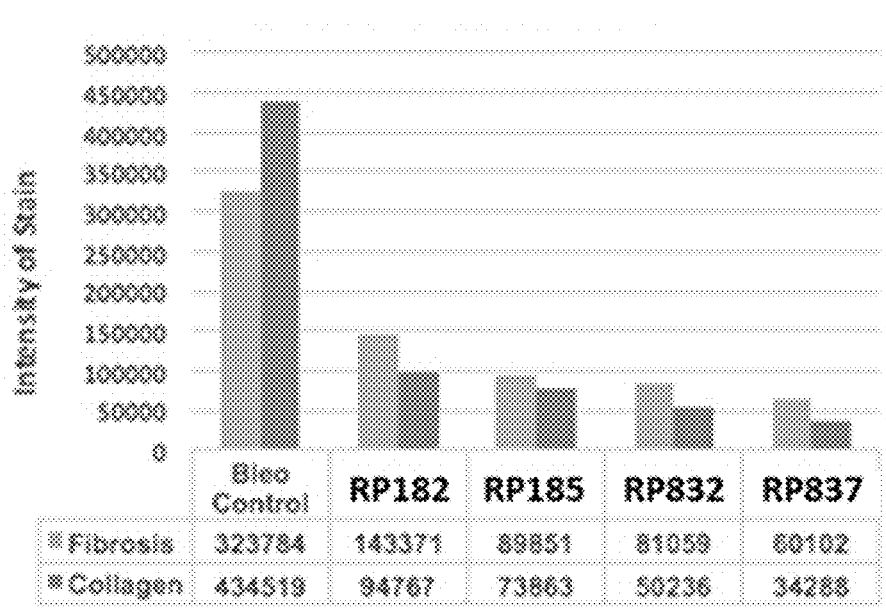
FIG. 1 shows a graph of results of reduction in bleomycin-induced lung fibrosis in a mouse model for lung fibrosis. The fibrosis measurements are Ashcroft scores following trichrome staining. Collagen scores are quantitative measurements following hydroxyproline staining. Further details are provided in the experimental section below.

The following description supplies specific details in order to provide a thorough understanding of the present invention. That said, to avoid obscuring aspects of the described immunomodulatory peptides and related methods of treating a subject, well-known structures, materials, processes, techniques, and operations are not shown or described in detail. Additionally, the skilled artisan will understand that the described immunomodulatory peptides and related methods of treating a subject can be implemented and used without employing these specific details. Indeed, the described immunomodulatory peptides and methods can be placed into practice by modifying the illustrated peptides, compositions, kits and methods, and can be used in conjunction with other methods, treatments, apparatuses, and techniques used conventionally.

Immunomodulatory Polypeptides

As summarized above, the present disclosure provides immune-modulatory peptides, particularly peptides that have immunosuppressive properties, and methods of administering such immune-modulatory peptides to a subject, particularly a subject suffering from a medical condition associated with persistent or chronic inflammation or at risk of developing such a medical condition. The terms "immune-modulatory" and "immunomodulatory" are used interchangeably herein. In some cases, an immunomodulatory peptide described herein can be referred to as an anti-inflammatory peptide and vice versa. In certain instances, the immunomodulatory peptide (e.g., as described herein) is an anti-inflammatory peptide, e.g., the peptide has at least one anti-inflammatory property.

Certain aspects of immunomodulatory polypeptides of interest which may be applied to, or adapted for use with, the peptides of the present disclosure are described by Jaynes et al. in WO2016/061133, the disclosure of which is herein incorporated by reference in its entirety.

The terms "peptide" and "polypeptide" are used synonymously herein to refer to polymers constructed from amino acid residues. The term "amino acid residue," as used herein, refers to any naturally occurring amino acid, non-naturally occurring amino acid, or amino acid mimetic (such as a peptoid monomer). An amino acid residue can be in an L- or D-form.

This disclosure includes immunomodulatory peptides having a striapathic region that comprises at least 25% of the length of the polypeptide and at least one immunomodulatory property. The term "striapathic region," refers to a region or portion of a peptide sequence that is composed of a sequence of alternating hydrophobic and hydrophilic modules. A "hydrophobic module" is a peptide sequence consisting of one to five (e.g., 1 to 3 or 1 to 2) hydrophobic amino acid residues, e.g., 1, 2, 3, 4 or 5 hydrophobic amino acid residues. A "hydrophilic module" is a peptide sequence consisting of one to five (e.g., 1 to 3 or 1 to 2) hydrophilic amino acid residues, e.g., 1, 2, 3, 4 or 5 hydrophilic amino acid residues.

A striapathic region can thus be represented by the formulae $(X_{1-5}J_{1-5})_n$ or $(J_{1-5}X_{1-5})_n$, where each X signifies a hydrophilic amino acid residue, each J signifies a hydrophobic amino acid residue, and each n is an integer from 1 to 10, such as 2 to 10, 2 to 8, 3 to 8, 4 to 8, or 5 to 10. As described in further detail below, aspects of the present disclosure include immunomodulatory peptides having a striapathic region having a specific degree of cationic charge Immunomodulatory peptides of this disclosure can include an striapathic region having a cationic surface. In certain embodiments, the striapathic region has a cationic charge (i.e., charge >0, e.g., +1, +2, +3, +4, +5, +6 or more). In certain embodiments, the immunomodulatory peptide includes a tail region (e.g., a hydrophobic tail sequence). In certain embodiments, an immunomodulatory peptide includes two or more striapathic regions. In such embodiments, two amphipathic regions of the peptide are in the form of a dimer, where the two amphipathic regions can have the same or different amino acid sequences (i.e., be a homodimer or a heterodimer). In certain embodiments, the two (or more) striapathic regions are connected via a linker or linking region. The linker can be a contiguous (or in-line) amino acid sequence or a non-amino acid moiety as desired.

Hydrophobic amino acid residues are characterized by a sidechain group that has predominantly non-polar chemical or physical properties, e.g., in an environment in which a peptide finds use, e.g., physiological conditions. Such hydrophobic amino acid residues can be naturally occurring or non-naturally occurring. A hydrophobic amino acid residue can be a mimetic of a naturally occurring amino acid that is characterized by a sidechain group that has predominantly non-polar chemical or physical properties. Conversely, hydrophilic amino acid residues are characterized by a sidechain group that is predominantly polar (e.g., charged or neutral hydrophilic), e.g., in an environment in which a peptide finds use, e.g., physiological conditions. Such hydrophilic amino acid residues can be naturally occurring or non-naturally occurring. A hydrophilic amino acid residues can be a mimetic of a naturally occurring amino acid characterized by a sidechain group that is predominantly hydrophilic (charged or neutral polar). Examples of hydrophilic and hydrophobic amino acid residues are shown in Table 1, below. Suitable non-naturally occurring amino acid residues and amino acid mimetics are known in the art. See, e.g., Liang et al. (2013), "An Index for Characterization of Natural and Non-Natural Amino Acids for Peptidomimetics," PLoS ONE 8(7):e67844.

Although most amino acid residues can be considered as either hydrophobic or hydrophilic, a few, depending on their context, can behave as either hydrophobic or hydrophilic. For example, due to their relatively weak non-polar characteristics, glycine, proline, serine and/or cysteine can sometimes function as hydrophilic amino acid residues. Conversely, due to their bulky, slightly hydrophobic side chains, histidine and arginine can sometimes function as hydrophobic amino acid residues.

TABLE 1

Hydrophobic and Hydrophilic Amino Acid Residues

| Hydrophilic Residues (X) | Hydrophobic Residues (J) |
|---|---|
| Arginine | Tryptophan |
| Histidine | Phenylalanine |
| Lysine | Tyrosine |
| Aspartic Acid | Isoleucine |
| Glutamic Acid | Leucine |
| Asparagine | Valine |
| Glutamine | Methionine |
| Pyrrolysine | Cysteine |
| Ornithine | Threonine |
| | Serine |
| | Alanine |
| | Proline |
| | Glycine |
| | Selenocysteine |
| | N-formylmethionine |
| | Norleucine |
| | Norvaline |

The term "anti-inflammatory property," as used herein, refers to any property of a polypeptide that can be evaluated in silico, in vitro, and/or in vivo, that reduces or inhibits, or would be expected to reduce or inhibit, a pro-inflammatory signal mediated by a protein target and/or reduces or inhibits inflammation in a subject. The term "immunomodulatory property," as used herein, refers to any property of a polypeptide that can be evaluated in silico, in vitro, and/or in vivo, that modulates, or would be expected to modulate, expression or secretion of one or more cytokines involved in autoimmunity and/or immune responses to infectious agents, or by modulating one or more components of a cytokine signalling pathway.

Selected Immunomodulatory Peptides of Interest

The exemplary immunomodulatory peptide sequences described herein are merely examples and are not the only immunomodulatory polypeptides provided herein. Indeed, fragments and variants of the sequences of the disclosed peptides are also within the scope of the present disclosure.

The present disclosure provides immunomodulatory polypeptides, sometimes referred to as "RP peptides," that satisfy one or more of the structural formulae described below. The present disclosure also provides immunomodulatory polypeptides that share a minimum degree of homology with any of the exemplary RP peptides disclosed herein, or variant thereof, or a fragment thereof. Thus, a peptide or polypeptide of the present disclosure is an immunomodulatory peptide that satisfies one of the formulae described herein or shares a minimum degree of homology with any of the exemplary RP peptides disclosed herein.

A "fragment" of the invention includes at least 4, 5, 6, 7, 8, 9, 10, 11, 12, 13, 14, 15, 16, 17, 18, 19, 20, 21, 22, or 23 contiguous amino acid residues of a peptide disclosed herein (or up to one less than the number of amino acid residues in the subject peptide) and retains at least one immunomodulatory property of the subject peptide. Thus, fragments of the invention include peptides that are missing one, two, three, four, or more amino acids from the N-terminus and/or the C-terminus relative to a parent immunomodulatory peptide disclosed herein.

A "variant" of the invention is a polypeptide that is substantially similar to a polypeptide disclosed herein and retains at least one immunomodulatory property of the subject polypeptide. Variants can include deletions (i.e., truncations) of one or more amino acid residues at the N-terminus or the C-terminus of a subject polypeptide disclosed herein; deletion and/or addition of one or more amino acid residues at one or more internal sites in the subject polypeptide disclosed herein; and/or substitution of one or more amino acid residues (e.g., one, two, three, or even more) at one or more positions in the subject polypeptide disclosed herein. For subject polypeptides that are 12 amino acid residues in length or shorter, variant polypeptides can include three or fewer (e.g., three, two, one, or none) deleted amino acid residues, whether located internally, at the N-terminal end, and/or at the C-terminal end.

Accordingly, the invention further provides immunomodulatory polypeptides that are at least 50% identical (i.e., at least 50% sequence identity) (e.g., at least 60%, at least 70%, at least 80%, at least 85%, at least 90%, at least 95% or more) to any one of the immunomodulatory polypeptides disclosed in Tables disclosed herein (e.g., Table 3) and still retain at least one immunomodulatory property. Sequence identity is based on a comparison of two peptide sequences or fragments thereof of the same or similar length.

As such, in certain embodiments, this disclosure provides polypeptides that include an amino acid sequence having from 1 to 10 amino acid differences (e.g., 10 or fewer, 9 or fewer, 8 or fewer, 7 or fewer, 6 or fewer, 5 or fewer, 4 or fewer, 3 or fewer, 2 or fewer, or 1 amino acid difference) to any one of the polypeptides disclosed herein and still retain at least one immunomodulatory property. An "amino acid difference" as used herein includes: an amino acid substitution, an amino acid insertion, a terminal amino acid addition, an amino acid deletion, a terminal amino acid truncation, or any combination thereof. The differences between the striapathic region of a homologous immunomodulatory polypeptide and any one of the immunomodulatory polypeptides of Table 3 can include deletions, additions, and/or substitutions of amino acid residues, as discussed herein. Substituted amino acid residues can be unrelated to the amino acid residue being replaced (e.g., unrelated in terms or hydrophobicity/hydrophilicity, size, charge, polarity, etc.), or the substituted amino acid residues can constitute similar, conservative, or highly conservative amino acid substitutions. As used herein, "similar," "conservative," and "highly conservative" amino acid substitutions are defined as shown in Table 2, below. The determination of whether an amino acid residue substitution is similar, conservative, or highly conservative is based exclusively on the side chain of the amino acid residue and not the peptide backbone, which may be modified to increase peptide stability, as discussed below.

TABLE 2

Classification of Amino Acid Substitutions

| Amino Acid in Subject Polypeptide | Similar Amino Acid Substitutions | Conservative Amino Acid Substitutions | Highly Conservative Amino Acid Substitutions |
|---|---|---|---|
| Glycine (G) | A, S, N | A | n/a |
| Alanine (A) | S, G, T, V, C, P, Q | S, G, T | S |
| Serine (S) | T, A, N, G, Q | T, A, N | T, A |
| Threonine (T) | S, A, V, N, M | S, A, V, N | S |
| Cysteine (C) | A, S, T, V, I | A | n/a |
| Proline (P) | A, S, T, K | A | n/a |
| Methionine (M) | L, I, V, F | L, I, V | L, I |
| Valine (V) | I, L, M, T, A | I, L, M | I |
| Leucine (L) | M, I, V, F, T, A | M, I, V, F | M, I |
| Isoleucine (I) | V, L, M, F, T, C | V, L, M, F | V, L, M |
| Phenylalanine (F) | W, Y, L, M, I, V | W, L | n/a |
| Tyrosine (Y) | F, W, H, L, I | F, W | F |
| Tryptophan (W) | F, L, V | F | n/a |
| Asparagine (N) | Q | Q | Q |
| Glutamine (Q) | N | N | N |
| Aspartic Acid (D) | E | E | E |
| Glutamic Acid (E) | D | D | D |
| Histidine (H) | R, K | R, K | R, K |
| Lysine (K) | R, H, O | R, H, O | R, O |
| Arginine (R) | K, H, O | K, H, O | K, O |
| Ornithine (O) | R, H, K | R, H, K | K, R |

Particular immunomodulatory peptide of interest, and fragments and variants thereof which find us in the subject pharmaceutical compositions and methods are now described in greater detail. In certain cases, the subject immunomodulatory peptides have macrophage modulating activity.

The "length" of a polypeptide is the number of amino acid residues linked end-to-end that constitute the polypeptide, excluding any non-peptide linkers and/or modifications that the polypeptide may contain. In some embodiments, the peptide is of 5 to 30 amino acid residues (e.g., 5 to 25, 10 to 20 or 5 to 18, 5 to 12 or 5 to 10, or 6 to 30, 6 to 25, 6 to 20, 6 to 18, 6 to 12, 6 to 10 or 7 to 12, or 7 to 10 amino acid residues) in length, and comprises a striapathic region of alternating hydrophilic and hydrophobic modules that adopts an amphipathic conformation under physiological conditions (e.g., as described herein). In some embodiments, the peptide is of 5 to 12 amino acid residues (e.g., 6, 7, 8, 9 or 10 amino acid residues) in length, and comprises a striapathic region of alternating hydrophilic and hydrophobic modules that adopts an amphipathic conformation under physiological conditions. In certain instances, a striapathic region of the peptide is of 5 to 18 amino acid residues in length (e.g., 6 to 18, 6 to 14, 6 to 12, 7 to 12, or 5, 6, 7, 8, 9, 10, 11 or 12 amino acids in length), wherein the peptide is optionally further modified (e.g., as described herein). The striapathic region can comprise: 2 or more (e.g., 3 or more or 4 or more) hydrophobic modules; and one or more (e.g., 2 or more, 3 or more, or 4 or more) hydrophilic modules (e.g., each comprising at least one cationic residue). In some embodiments, the subject immunomodulatory peptides (e.g., as described herein) are CD206-binding peptides. In some instances, the striapathic region of the peptide has a length of 6 to 12 amino acid residues, such as 7 to 12. In some instances, the striapathic region of the peptide has a length of 6 to 10 amino acid residues.

The hydrophobic modules can consist of any convenient residues. In certain instances, the hydrophobic modules include amino acid residues selected from phenylalanine, tryptophan, alanine, valine, and glycine. The striapathic region can include 1, 2 or more cationic amino acid residues in total, such as 3 or more, 4 or more, 5 or more, 6 or more, or even more. The immunomodulatory peptide can comprise 2, 3 or more hydrophilic modules that consist of any convenient residues. In some instances, the hydrophilic modules include amino acid residues selected from lysine, arginine, histidine, aspartic acid, glutamic acid, asparagine and glutamine.

In the formula described herein, J(N) is used to refer to a particular hydrophobic module, where N is indicates a position within the linear formula. Similarly, X(N) is used to refer to a particular hydrophilic module, where N is indicates a position within the linear formula.

In the formula described herein, $J_{(nx)}$ is used to refer to a particular hydrophobic amino acid residue, where n indicates which module the residue is located in and x indicates its position within the module. Similarly, $X_{(nx)}$ is used to refer to a particular hydrophilic amino acid residue, where n indicates which module the residue is located in and x indicates its position within the module.

In certain instances of the immunomodulatory peptide, the striapathic region comprises hydrophobic and hydrophilic modules having the following formula:

[J1]-[X1]-[J2]     (formula 1).

In some embodiments of the immunomodulatory peptide, the striapathic region comprises the following formula of hydrophilic and hydrophobic modules:

[J1]-[X1]-[J2]-[X2]     (formula 2)

In some embodiments of the immunomodulatory peptide, the striapathic region comprises the following formula of hydrophilic and hydrophobic modules:

[X1]-[J1]-[X2]-[J2]     (formula 3).

In some embodiments of the immunomodulatory peptide, the striapathic region comprises the following formula of hydrophobic and hydrophilic modules:

[J1]-[X1]-[J2]-[X2]-[J3]     (formula 4).

In certain embodiments, the striapathic region comprises three or more hydrophilic modules and three or more hydrophobic modules and comprises one of the following formulae:

[J1]-[X1]-[J2]-[X2]-[J3]-[X3]     (formula 5)

[J1]-[X1]-[J2]-[X2]-[J3]-[X3]-[J4]     formula 6).

In certain embodiments, the striapathic region comprises three or more hydrophilic modules and three or more hydrophobic modules and comprises one of the following formulae:

[X1]-[J1]-[X2]-[J2]-[X3]-[J3]     (formula 7).

In some cases of formula 1, the striapathic region has a sequence defined by one of the formulae:

$[J_{1a}J_{1b}]-[X_{1a}X_{1b}]-[J_{2a}J_{2b}]$     (formula 1A); and $[J_{2b}J_{2a}]-[X_{1b}X_{1a}]-[J_{1b}J_{1a}]$     (formula 1B);

wherein:

$J_{1a}$, $J_{1b}$, $J_{2a}$ and $J_{2b}$ are each independently selected from a hydrophobic amino acid residue (e.g., phenylalanine, tryptophan and valine); and $X_{1a}$ and $X_{1b}$ are each independently selected from a hydrophilic amino acid residue (e.g., lysine or arginine).

In some instances of formula 1A, the peptide includes the sequence FWKRFV (RP837N) (SEQ ID NO: 5), or a fragment or variant thereof (e.g., a variant including one substitution).

In some embodiments of formula 2, the striapathic region has a sequence defined by the formula:

$[J_{1a}J_{1b}]-[X_{1a}X_{1b}]-[J_{2a}]-[X_{2a}]$     (formula 2A);

wherein:

$J_{1a}$, $J_{1b}$, and $J_{2a}$ are each independently selected from a hydrophobic amino acid residue (e.g., phenylalanine, tryptophan or valine); and $X_{1a}$, $X_{1b}$ and $X_{2a}$ are each independently selected from a hydrophilic amino acid residue (e.g., lysine or arginine).

In some instances of formula 2A, the peptide includes the sequence FVRKWR (RP837C) (SEQ ID NO: 6), or a fragment or variant thereof (e.g., a variant including one substitution).

In some embodiments of formula 3, the striapathic region has a sequence defined by the formula:

$[X_{1a}X_{1b}]-[J_{1a}J_{1b}J_{1c}J_{1d}]-[X_{2a}X_{2b}]-[J_{2a}J_{2b}]$     (formula 3A);

wherein:

$J_{1a}$, $J_{1b}$, $J_{1c}$, $J_{1d}$, $J_{2a}$ and $J_{2b}$ are each independently selected from a hydrophobic amino acid residue (e.g., leucine, serine, alanine or phenylalanine); and $X_{1a}$, $X_{1b}$, $X_{2a}$ and $X_{2b}$ are each independently selected from a hydrophilic amino acid residue (e.g., glutamic acid, aspartic acid, lysine, asparagine or arginine).

In some embodiments of formula 3A, the striapathic region has a sequence defined by the formula:

$EX_{1b}LSAFX_{2a}NJ_{2a}J_{2b}$     (SEQ ID NO: 25);

wherein:

$J_{2a}$ and $J_{2b}$ are each independently selected from alanine and phenylalanine; and $X_{1b}$ and $X_{2a}$ are each independently selected from lysine and arginine.

In some instances of formula 3A, the peptide includes the sequence EKLSAFRNFF (RP843) (SEQ ID NO: 9), or a fragment or variant thereof (e.g., a variant including one or two substitutions).

In certain instances of formula 4, the striapathic region has a sequence defined by one of the formulae:

$[J_{1a}J_{1b}]-[X_{1a}X_{1b}]-[J_{2a}J_{2b}]-[X_{2a}X_{2b}]-[J_{3a}J_{3b}]$     (formula 4A); and $[J_{3a}J_{3b}]-[X_{2a}X_{2b}]-[J_{2b}J_{2a}]-[X_{1b}X_{1a}]-[J_{1b}J_{1a}]$     (formula 4B);

wherein:

$J_{1a}$, $J_{1b}$, $J_{2a}$, $J_{2b}$, $J_{3a}$ and $J_{3b}$ are each independently selected from a hydrophobic amino acid residue (e.g., phenylalanine, tyrosine, isoleucine or leucine); and $X_{1a}$, $X_{1b}$, $X_{2a}$ and $X_{2b}$ are each independently selected from a hydrophilic amino acid residue (e.g., lysine or arginine).

In some embodiments of formula 4A-4B, the striapathic region has a sequence defined by the formula:

$LJ_{1b}KKIIKKJ_{3a}L$     (SEQ ID NO: 26)

wherein $J_{1b}$ and $J_{3a}$ are independently phenylalanine, tyrosine or leucine (e.g., tyrosine or leucine).

In some instances of formula 4A-4B, the peptide includes the sequence LYKKIIKKLL (RP846) (SEQ ID NO: 12), or a fragment or variant thereof (e.g., a variant including one or two substitutions).

In some embodiments of formula 4, the striapathic region has a sequence defined by one of the formulae:

$$[J_{1a}J_{1b}J_{1c}[X_{1a}]J_{2a}J_{2b}]-[X_{2a}X_{2b}]-[J_{3a}J_{3b}]$$ (formula 4C);

wherein:

$J_{1a}$, $J_{1b}$, $J_{1c}$, $J_{2a}$, $J_{2b}$, $J_{3a}$, and $J_{3b}$ are each independently selected from a hydrophobic amino acid residue (e.g., phenylalanine, tyrosine or proline); and $X_{1a}$, $X_{2a}$ and $X_{2b}$ are each independently selected from a hydrophilic amino acid residue (e.g., aspartic acid, lysine or arginine).

In some embodiments of formula 4C, the striapathic region has a sequence defined by the formula:

$$FYPDJ_{2a}J_{2b}X_{2a}X_{2b}J_{3a}J_{3b}$$ (SEQ ID NO: 27)

wherein $J_{2a}$, $J_{2b}$, $J_{1a}$, and $J_{3b}$ are each independently phenylalanine or tyrosine (e.g., phenylalanine) $X_{2a}$ and $X_{2b}$ are each independently lysine or arginine In some instances of formula 4C, the peptide includes the sequence FYPDFFKKFF (RP844) (SEQ ID NO: 10), or a fragment or variant thereof (e.g., a variant including one or two substitutions).

In some embodiments of formula 4, the striapathic region has a sequence defined by one of the formulae:

$$[J_{1a}J_{1b}]-[X_{1a}X_{1b}]-[J_{2a}]-[X_{2a}X_{2b}X_{2c}]-[J_{3a}J_{3b}]$$ (formula 4D);

wherein:

$J_{1a}$, $J_{1b}$, $J_{2a}$, $J_{1a}$ and $J_{3b}$ are each independently selected from a hydrophobic amino acid residue (e.g., phenylalanine, serine, glycine or isoleucine); and $X_{1a}$, $X_{1b}$, $X_{2a}$, $X_{2b}$ and $X_2$ are each independently selected from a hydrophilic amino acid residue (e.g., glutamic acid, aspartic acid, lysine or arginine).

In some embodiments of formula 4D, the striapathic region has a sequence defined by the formula:

$$J_{1a}J_{1b}X_{1a}X_{1b}SKEKIG$$ (SEQ ID NO: 28)

wherein:

$J_{1a}$ and $J_{1b}$ are each independently phenylalanine or tyrosine (e.g., phenylalanine); and $X_{1a}$ and $X_{1b}$ are each independently lysine or arginine.

In some instances of formula 4D, the peptide includes the sequence FFRKSKEKIG (RP853) (SEQ ID NO: 18), or a fragment or variant thereof (e.g., a variant including one or two substitutions).

In certain instances, the striapathic region has a sequence defined by the formula:

$$[J_{1a}J_{1b}]-[X_{1a}X_{1b}]-[J_{2a}J_{2b}]-[X_{2a}X_{2b}]-[J_{3a}]$$ (formula 4E)

wherein:

$J_{1a}$, $J_{1b}$, $J_{2a}$, $J_{2b}$ and $J_{3a}$ are each independently selected from phenylalanine, alanine and isoleucine; and $X_{1a}$, $X_{1b}$, $X_{2a}$, $X_{2b}$ and $X_2$ are each independently selected from ornithine, lysine and arginine.

In certain instances, the striapathic region has a sequence defined by the formula:

$$[J_{1a}J_{1b}]-[X_{1a}X_{1b}]-[J_{2a}J_{2b}]-[X_{2a}X_{2b}]-[J_{3a}]-[X_{3a}]$$ (formula 5A)

wherein:

$J_{1a}$, $J_{1b}$, $J_{2a}$, $J_{2b}$ and $J_{3a}$ are each independently selected from phenylalanine, tryptophan, alanine and valine; and $X_{1a}$, $X_{1b}$, $X_{2a}$, $X_{2b}$ and $X_{3a}$ are each independently selected from ornithine, lysine and arginine.

In some embodiments of formula 5A, the striapathic region has a sequence defined by the formula:

$$J_{1a}J_{1b}OOJ_{2a}J_{2b}OOJ_{3a}O$$ (SEQ ID NO: 29)

wherein $J_{1a}$, $J_{1b}$, $J_{2a}$, $J_{2b}$ and $J_{3a}$ are each independently selected from phenylalanine and alanine (e.g., each J1, J2 and J3 module includes both phenylalanine and alanine).

In some embodiments of formula 5A, the striapathic region has a sequence defined by the formula:

$$FAX_{1a}X_{1b}FAX_{2a}X_{2b}J_{3a}FX_{3a}$$ (SEQ ID NO: 30)

wherein $X_{1a}$, $X_{1b}$, $X_{2a}$, $X_{2b}$ and $X_{3a}$ are each independently selected from ornithine, lysine and arginine.

In some instances of formula 5A, the peptide includes the sequence FAOOFAOOFO (RP850) (SEQ ID NO: 19), or a fragment or variant thereof (e.g., a variant including one or two substitutions).

In some embodiments of formula 5A, the striapathic region has a sequence defined by the formula:

$$FWKX_{1b}FVX_{2a}KWX_{3a}$$ (SEQ ID NO: 31)

wherein $X_{1b}$, $X_{2a}$ and $X_{3a}$ are each independently lysine or arginine.

In some instances of formula 5A, the peptide includes the sequence FWKRFVRKWR (RP837) (SEQ ID NO: 4) or FWKKFVKKWK (RP841) (SEQ ID NO: 7), or a fragment or variant thereof (e.g., a variant including one or two substitutions).

In some cases, the immunomodulatory peptide of formula 5A is not FFRKFAKRFK (RP183) (SEQ ID NO: 21) or FFKKFFKKFK (RP185) (SEQ ID NO: 22).

In certain instances, the striapathic region has a sequence defined by the formula:

$$[J_{1a}J_{1b}]-[X_{1a}X_{1b}]-[J_{2a}J_{2b}]-[X_{2a}X_{2b}]-[J_{3a}]-[X_{3a}]$$ (formula 5A)

wherein:

$J_{1a}$, $J_{1b}$, $J_{2a}$, $J_{2b}$ and $J_{3a}$ are each independently selected from a hydrophobic amino acid residue (e.g., phenylalanine, tryptophan, alanine, valine, and glycine); and $X_{1a}$, $X_{1b}$, $X_{2a}$, $X_{2b}$ and $X_{3a}$ are each independently selected from a hydrophilic amino acid residue (e.g., lysine, ornithine, arginine, histidine, aspartic acid, glutamic acid, asparagine or glutamine.

In some cases of formula 5A, $J_{1a}$, $J_{1b}$, $J_{2a}$, $J_{2b}$ and $J_{3a}$ are each independently selected from phenylalanine, tryptophan, alanine and glycine; and $X_{1a}$, $X_{1b}$, $X_{2a}$, $X_{2b}$ and $X_{3a}$ are each independently selected from lysine and arginine. In certain instances of formula 5A, $J_{1a}$, $J_{1b}$, $J_{2a}$, $J_{2b}$ and $J_{3a}$ are each independently selected from phenylalanine, tryptophan, alanine and valine; and $X_{1a}$, $X_{1b}$, $X_{2a}$, $X_{2b}$ and $X_{3a}$ are each independently selected from ornithine, lysine and arginine (e.g., Lys or Arg). In some instances of formula 5A, $J_{1a}$, $J_{1b}$, $J_{2a}$, $J_{2b}$ and $J_{3a}$ are each independently selected from phenylalanine and alanine; and $X_{1a}$, $X_{1b}$, $X_{2a}$, $X_{2b}$ and $X_{3a}$ are each independently selected from lysine and arginine. In certain cases of formula 5A, $J_{1a}$, $J_{1b}$, $J_{2a}$, $J_{2b}$ and $J_{3a}$ are each phenylalanine; and $X_{1a}$, $X_{1b}$, $X_{2a}$, $X_{2b}$ and $X_{3a}$ are each independently selected from lysine and arginine. In some cases of formula 5A, $J_{1a}$, $J_{1b}$, $J_{2a}$, $J_{2b}$ and $J_{3a}$ are each tryptophan; and $X_{1a}$, $X_{1b}$, $X_{2a}$, $X_{2b}$ and $X_{3a}$ are each independently selected from histidine, lysine and arginine. In some instances of formula 5A, $J_{1a}$, $J_{2a}$ and $J_{3a}$ are each independently selected from phenylalanine and tryptophan, $J_{1b}$ is selected from tryptophan and alanine, $J_{2b}$ is selected from valine, tryptophan and alanine and each of $X_{1a}$, $X_{1b}$, $X_{2a}$, $X_{2b}$ and $X_{3a}$ are independently selected from ornithine, lysine, arginine or histidine.

In some embodiments of formula 5A, the striapathic region has a sequence defined by the formula:

$$WWX_{1a}HWWHX_{2b}WX_{3a}$$ (SEQ ID NO: 32)

wherein $X_{1a}$, $X_{2b}$ and $X_{3a}$ are each independently histidine, lysine or arginine.

In some instances of formula 5B, the peptide includes the sequence WWHHWWHHWH (RP847) (SEQ ID NO: 13), WWRHWWHRWR (RP848) (SEQ ID NO: 14) or WWKH-WWHKWK (RP849) (SEQ ID NO: 15), or a fragment or variant thereof (e.g., a variant including one or two substitutions).

In some embodiments of formula 5, the striapathic region has a sequence defined by the formula:

$$[J_{1a}J_{1b}]-[X_{1a}X_{1b}]-[J_{2a}J_{2b}J_{2c}]-[X_{2b}]-[J_{3a}]-[X_{3a}] \quad \text{(formula 5B)};$$

wherein:

$J_{1a}$, $J_{1b}$, $J_{2a}$, $J_{2b}$ and $J_{3a}$ are each independently selected from a hydrophobic amino acid residue (e.g., phenylalanine, alanine, threonine or leucine); and $X_{1a}$, $X_{1b}$, $X_{2a}$, $X_{2b}$ and $X_{3a}$ are each independently selected from a hydrophilic amino acid residue (e.g., histidine, aspartic acid, lysine or arginine).

In some embodiments of formula 5B, the striapathic region has a sequence defined by the formula:

$$J_{1a}J_{1b}X_{1a}HJ_{2a}J_{2b}THLD \quad \text{(SEQ ID NO: 33)}$$

wherein;

$J_{1a}$, $J_{1b}$, $J_{2a}$ and $J_{2b}$ are each independently selected from phenylalanine and alanine; and $X_{1a}$ is independently selected from lysine and arginine.

In some instances of formula 5C, the peptide includes the sequence FFRHFATHLD (RP845) (SEQ ID NO: 11), or a fragment or variant thereof (e.g., a variant including one or two substitutions).

In some embodiments of formula 5, the striapathic region has a sequence defined by one of the formulae:

$$[J_{1a}]-[X_{1a}]-[J_{2a}J_{2b}J_{2c}]-[X_{2a}]-[J_{3a}J_{3b}]-[X_{3a}X_{3b}] \quad \text{(formula 5C)};$$

wherein:

$J_{1a}$, $J_{2a}$, $J_{2b}$, $J_{2c}$, $J_{3a}$, and $J_{3b}$ are each independently selected from a hydrophobic amino acid residue (e.g., phenylalanine, tyrosine, leucine, glycine or isoleucine); and $X_{1a}$, $X_{2a}$, $X_{3a}$ and $X_{3b}$ are each independently selected from a hydrophilic amino acid residue (e.g., glutamine, lysine or histidine).

In some embodiments of formula 5C, the striapathic region has a sequence defined by the formula:

$$J_{1a}QJ_{2a}LGX_{2a}IIHH \quad \text{(SEQ ID NO: 34)}$$

wherein:

$J_{1a}$ and $J_{2a}$ are each independently selected from phenylalanine, tyrosine and leucine; and $X_{2a}$ is lysine and arginine.

In some instances of formula 5C, the peptide includes the sequence FQFLGKIIHH (RP852) (SEQ ID NO: 17), or a fragment or variant thereof (e.g., a variant including one or two substitutions).

In some embodiments of formula 6, the striapathic region has a sequence defined by the formula:

$$[J_{1a}]-[X_{1a}X_{1b}]-[J_{2a}J_{2b}]-[X_{2a}]-[J_{3a}]-[X_{3a}X_{3b}]-[J_{4a}J_{4b}] \quad \text{(formula 6A)};$$

wherein:

$J_{1a}$, $J_{2a}$, $J_{2b}$, $J_{3a}$ $J_{4a}$, and $J_{4b}$ are each independently selected from a hydrophobic amino acid residue (e.g., phenylalanine, tryptophan, alanine, isoleucine, valine, and glycine); and $X_{1a}$, $X_{1b}$, $X_{2a}$, $X_{3a}$ and $X_{3b}$ are each independently selected from a hydrophilic amino acid residue (e.g., lysine, arginine, histidine, aspartic acid, glutamic acid, asparagine or glutamine).

In some embodiments of formula 6A, the striapathic region has a sequence defined by the formula:

$$GX_{1a}X_{1b}GJ_{2b}X_{2a}GX_{3a}X_{3b}GJ_{4b} \quad \text{(SEQ ID NO: 35)}$$

wherein:

$J_{2b}$ and $J_{4b}$ are each independently selected from phenylalanine, tryptophan, alanine, isoleucine and valine; and $X_{1a}$, $X_{1b}$, $X_{2a}$, $X_{3a}$ and $X_{3b}$ are each independently selected from lysine, arginine, histidine, aspartic acid, glutamic acid, asparagine and glutamine.

In some embodiments of formula 6A, the striapathic region has a sequence defined by the formula:

$$GDX_{1b}GIX_{2a}GHX_{3b}GF \quad \text{(SEQ ID NO: 36)}$$

wherein $X_{1b}$, $X_{2a}$ and $X_{3b}$ are each independently selected from lysine and arginine.

In some instances of formula 6A, the peptide includes the sequence GDRGIKGHRGF (RP842) (SEQ ID NO: 8), or a fragment or variant thereof (e.g., a variant including one or two substitutions).

In some embodiments of formula 7, the striapathic region has a sequence defined by one of the formulae:

$$[X_{1a}X_{1b}]-[J_{1a}]-[X_{2a}]-[J_{2a}]-[X_{3a}]-[J_{3a}J_{3b}J_{3c}] \quad \text{(formula 7A)};$$

wherein:

$J_{1a}$, $J_{2a}$, $J_{3a}$, $J_{3b}$, and $J_{3c}$ are each independently selected from a hydrophobic amino acid residue (e.g., isoleucine, valine, leucine, serine or alanine); and $X_{1a}$, $X_{1b}$, $X_{2a}$ and $X_{3a}$ are each independently selected from a hydrophilic amino acid residue (e.g., lysine or arginine).

In some embodiments of formula 7A, the striapathic region has a sequence defined by the formula:

$$X_{1a}X_{1b}IX_{2a}VX_{3a}LSA \quad \text{(SEQ ID NO: 37)}$$

wherein $X_{1a}$, $X_{1b}$, $X_{2a}$ and $X_{3a}$ are each independently selected from lysine and arginine.

In some instances of formula 7A, the peptide includes the sequence KKIRVRLSA (RP851) (SEQ ID NO: 16), or a fragment or variant thereof (e.g., a variant including one or two substitutions).

Multimeric Peptides

This disclosure includes a multimer (e.g., a dimer) of two or more immunomodulatory peptides (e.g., as described herein) connected via a branced or liner linker. Aspects of the present disclosure include dimers of any of the subject immunomodulatory polypeptides. The dimers can be homodimers or heterodimers. Any two immunomodulatory polypeptides can be connected via a linker. Any convenient linker can be utilized. Linkers that may be employed include, but are not limited to, covalent bonds, peptide linkers (e.g., a glycine containing linker or a Gly and Ser containing linker), C1-C12 linkers having terminal amino and or carboxylic acid groups, or polymer linkers (e.g., a PEG or modified PEG). The dimers can include a linker that connects the C-terminal of a first polypeptide with the N-terminal of a second polypeptide. In certain cases, the two polypeptides can be linked via the C-terminals. In certain instances, the two polypeptides can be linked via the N-terminals.

The present disclosure further includes any two immunomodulatory polypeptides which have been linked together. The linkage can be formed by a peptide linker, such as a Gly-Gly-Gly (GGG), Gly-Gly-Gly-Arg (GGGR; SEQ ID NO: 40), Gly-Pro-Gly (GPG), or Gly-Pro-Gly-Arg (GPGR; SEQ ID NO: 41) sequence, that links the C-terminal end of a first immunomodulatory polypeptide to the N-terminal end of a second immunomodulatory polypeptide. Alternatively, the linkage can be a peptoid linker (e.g., a poly N-substituted version of any of the foregoing peptide linkers), a polymer containing g-amino acids (e.g., corresponding to any of the foregoing peptide linkers), or a non-peptide, chemical linker. The linked immunomodulatory polypeptides can be any of the polypeptides disclosed herein (e.g., in Table 3), and can include the same polypeptide being linked to form a homodimer or different polypeptides being linked to form a heterodimer. Techniques for linking peptides via peptide and non-peptide linkers are well known in the art, and the inventive polypeptide combinations are intended to encompass all such linkages.

Any two striapathic region-containing peptides (e.g., as described herein) can be linked. The two regions of a dimeric peptide can be homodimeric or heterodimeric with respect to each other. By homodimeric is meant the two peptide regions of the dimeric peptide have the same N to C sequence or a reversed C to N sequence thereof. The subject immunomodulatory polypeptides described herein can be linked in any convenient configuration to produce a multimer. In certain instances, the multimer includes 3 or more immunomodulatory polypeptides (e.g., as described herein), where the polypeptides can be arranged in a linear or branched fashion. A linear multimer of immunomodulatory polypeptides can include head to tail arrangement of linked peptides, linked via a covalent bond or an optional linker (e.g., a peptidic linker). In some instances, a linear multimer can be referred to as an oligomer, e.g., a polypeptide chain that includes sequence segments of an immunomodulatory polypeptides (e.g., as described herein). Alternatively, the immunomodulatory polypeptides of a linear multimer can be linked via a head to head (e.g., N-terminal to N-terminal linked) and/or tail to tail (e.g., C-terminal to C-terminal linked) configurations. In branched multimers the immunomodulatory polypeptides can be linked via any convenient branched linker, e.g., a group that includes three functional groups for attached to amino acid residues, such as a lysine amino acid. In some cases, the multimer is a dimer.

In certain cases the immunomodulatory peptide dimer has the formula:

$$Z^1\text{-}T\text{-}Z^2$$

wherein:
T is a linker, e.g., a peptide linker;
$Z^1$ is a first polypeptide or region of 3-10 (e.g., 4-10, 5-10, or 3-6 or 3, 4, 5, or 6) amino acid residues consisting of a mixture of hydrophilic amino acid resides and hydrophobic amino acid residues (e.g. as described herein); and
$Z^2$ is a second polypeptide or region of 3-10 (e.g., 4-10, 5-10, or 3-6 or 3, 4, 5, or 6) amino acid residues consisting of a mixture of hydrophilic amino acid resides and hydrophobic amino acid residues (e.g. as described herein).

In certain cases of the dimer, the hydrophilic modules consist of amino acid residues selected from lysine and arginine; and the hydrophobic modules consist of amino acid residues selected from phenylalanine and tryptophan. In certain instances the first and second polypeptides ($Z^1$ and $Z^2$) comprise four amino acid residues. In certain cases each of $Z^1$ and $Z^2$ comprises four amino acid residues, wherein two amino acid residues are hydrophilic residues (e.g. as described herein) and the remaining two amino acid resides are hydrophobic residues (e.g. as described herein).

In certain embodiments, the dimer has one of the following formulae:

[X1]-[J1]-T-[J1]-[X1]     (formula 8)

[J1]-[X1]-T-[X1]-[J1]     (formula 9)

[X1]-[J1]-T-[J2]-[X2]     (formula 10)

[J1]-[X1]-T-[X2]-[J2]     (formula 11)

wherein T is the linker (e.g., peptide linker).

In some cases of formula 8 and 9, the dimer has a sequence defined by one of the following formulae:

[$X_{1a}X_{1b}$]-[$J_{1a}J_{1b}$]-T-[$J_{1b}J_{1a}$]-[$X_{1b}X_{1a}$]     (formula 8A); or

[$J_{1a}J_{1b}$]-[$X_{1a}X_{1b}$]-T-[$X_{1b}X_{1a}$]-[$J_{1b}J_{1a}$]     (formula 9A);

wherein:
T is the peptide linker (e.g., a polyglycine linker);
$J_{1a}$ and $J_{1b}$ are each independently selected from a hydrophobic amino acid residue (e.g. tryptophan or phenylalanine); and
$X_{1a}$ and $X_{1b}$ are each independently selected from a hydrophilic amino acid residue (e.g., asparagine or arginine). In certain instances of formula 8A and 9A, T is a peptide linker consisting of one, two or three glycine residues.

In some embodiments of formula 9A, the dimer has a sequence defined by the formula:

FW-[$X_{1a}X_{1b}$]-T-[$X_{1b}X_{1a}$]-WF     (SEQ ID NO: 38)

wherein $X_{1a}$, $X_{1b}$ are each independently selected from lysine and arginine.

In some embodiments of formula 9A, the dimer has a sequence defined by the formula:

[$J_{1a}J_{1b}$]-KR-T-RK-[$J_{1b}J_{1a}$]     (SEQ ID NO: 39)

wherein $J_{1a}$ and $J_{1b}$, are each independently selected from tryptophan and phenylalanine.

In some instances of formula 7A, the peptide includes the sequence FWKRGGRKWF (RP837A) (SEQ ID NO: 4), or a fragment or variant thereof (e.g., a variant including one or two substitutions).

In some cases of formula 10 and 11, the dimer has a sequence defined by one of the following formulae:

[$J_{1a}J_{1b}$]-[$X_{1a}X_{1b}$]-T-[$X_{2a}X_{2b}$]-[$J_{2a}J_{2b}$]     (formula 10A)

[$X_{1a}X_{1b}$]-[$J_{1a}J_{1b}$]-T-[$J_{2a}J_{2b}$]-[$X_{2a}X_{2b}$]     (formula 11A)

wherein:
$J_{1a}$, $J_{1b}$, J2a and $J_{2b}$ are each independently selected from a hydrophobic amino acid residue (e.g. tryptophan or phenylalanine); and
$X_{1a}$, $X_{1b}$, $X_{2a}$ and $X_{2b}$ are are each independently selected from a hydrophilic amino acid residue (e.g., asparagine or arginine). In certain instances of formula 10A and 11A, T is a peptide linker consisting of one, two or three glycine residues.

In certain instances, the first and second polypeptides ($Z^1$ and $Z^2$) of the dimer comprise one of the following formulae of hydrophilic and hydrophobic modules: [X1]-[J1]-[X2]-[J2] (formula 3); or [J1]-[X1]-[J2]-[X2] (formula 2).

In certain embodiments, the dimer has one of the following formulae:

[X1]-[J1]-[X2]-[J2]-T-[J2]-[X2]-[J1]-[X1]     (formula 12);

[J1]-[X1]-[J2]-[X2]-T-[X2]-[J2]-[X1]-[J1]     (formula 13);

[X1]-[J1]-[X2]-[J2]-T-[J3]-[X3]-[J4]-[X4]     (formula 14);

[J1]-[X1]-[J2]-[X2]-T-[X3]-[J3]-[X4]-[J4]     (formula 15);

wherein T is the peptide linker.

In some instances of formula 12 and 13, the dimer has one of the following formulae:

$$[X_{1a}]\text{-}[J_{1a}]\text{-}[X_{2a}]\text{-}[J_{2a}]\text{-}T\text{-}[J_{2a}]\text{-}[X_{2a}]\text{-}[J_{1a}]\text{-}[X_{1a}] \quad \text{(formula 12A); and}$$

$$[J_{1a}]\text{-}[X_{1a}]\text{-}[J_{2a}]\text{-}[X_{2a}]\text{-}[X_{2a}]\text{-}[J_{2a}]\text{-}[X_{1a}]\text{-}[J_{1a}] \quad \text{(formula 13A);}$$

wherein:

T is the peptide linker (e.g., a polyglycine linker);

$J_{1a}$ and $J_{2a}$ are each independently selected from phenylalanine and tryptophan; and $X_{1a}$ and $X_{2a}$ are each independently selected from lysine and arginine.

In some instances of formula 12A, the peptide includes the sequence RWKFGGFKWR (RP832C) (SEQ ID NO: 1), or a fragment or variant thereof (e.g., a variant including one or two substitutions).

In some instances of formula 13A, the peptide includes the sequence FKWRGGRWKF (RP837C) (SEQ ID NO: 3), or a fragment or variant thereof (e.g., a variant including one or two substitutions). In certain embodiments, an immunomodulatory peptide includes a tail region.

In some instances of formula 14 and 15, the dimer has one of the following formulae:

$$[X_{1a}]\text{-}[J_{1a}]\text{-}[X_{2a}]\text{-}[J_{2a}]\text{-}T\text{-}[J_{3a}]\text{-}[X_{3a}]\text{-}[J_{4a}]\text{-}[X_{4a}] \quad \text{(formula 14A); and}$$

$$[J_{1a}]\text{-}[X_{1a}]\text{-}[J_{2a}]\text{-}[X_{2a}]\text{-}[X_{3a}]\text{-}[J_{3a}]\text{-}[X_{4a}]\text{-}[J_{4a}] \quad \text{(formula 15A);}$$

wherein:

T is the peptide linker (e.g., a polyglycine linker);

$J_{1a}$, $J_{2a}$, $J_{1a}$, and $J_{4a}$ are each independently selected from phenylalanine and tryptophan; and $X_{1a}$, $X_{2a}$, $X_{3a}$ and $X_{4a}$ are each independently selected from lysine and arginine.

Immunomodulatory peptides of interest include, but are not limited to, any one of the polypeptides of Table 3, a fragment thereof (e.g., as described herein), or a variant thereof (e.g., as described herein).

TABLE 3 selected peptides of interest

| RP# | SEQ ID NO: | Sequence |
|---|---|---|
| 832C | 1 | RWKFGGFKWR |
| 837 | 2 | FWKRFVRKWR |
| 837C | 3 | FKWRGGRWKF |
| 837A | 4 | FWKRGGRKWF |
| 837N | 5 | FWKRFV |
| 837C[1] | 6 | FVRKWR |
| 841 | 7 | FWKKFVKKWK |
| 842 | 8 | GDRGIKGHRGF |
| 843 | 9 | EKLSAFRNFF |
| 844 | 10 | FYPDFFKKFF |
| 845 | 11 | FFRHFATHLD |
| 846 | 12 | LYKKIIKKLL |
| 847 | 13 | WWHHWWHHWH |
| 848 | 14 | WWRHWWHRWR |
| 849 | 15 | WWKHWWHKWK |
| 851 | 16 | KKIRVRLSA |
| 852 | 17 | FQFLGKIIHH |
| 853 | 18 | FFRKSKEKIG |
| 850 | 19 | FAOOFAOOFO |

In certain embodiments, the subject immunomodulatory polypeptide includes a sequence selected from:

a) a sequence selected from the peptide sequences of Table 3;

b) a sequence having at least 75% sequence identity (e.g., at least 80%, at least 85%, at least 90% or at least 95% sequence identity) with the sequence defined in a); and c) a sequence having one or two amino acid substitutions relative to the sequence defined in a), wherein the one or two amino acid substitutions are substitutions for amino acids according to Table 2 (e.g., a similar amino acid substitution, a conservative amino acid substitutions or a highly conservative amino acid substitution).

In certain cases, the sequence set forth in a) is RP 832C. In certain cases, the sequence set forth in a) is RP 837. In certain cases, the sequence set forth in a) is RP 837C. In certain cases, the sequence set forth in a) is RP 837A. In certain cases, the sequence set forth in a) is RP 837N. In certain cases, the sequence set forth in a) is RP 837C[1]. In certain cases, the sequence set forth in a) is RP 841. In certain cases, the sequence set forth in a) is RP 842. In certain cases, the sequence set forth in a) is RP 843. In certain cases, the sequence set forth in a) is RP 844. In certain cases, the sequence set forth in a) is RP 845. In certain cases, the sequence set forth in a) is RP 846. In certain cases, the sequence set forth in a) is RP 847. In certain cases, the sequence set forth in a) is RP 848. In certain cases, the sequence set forth in a) is RP 849. In certain cases, the sequence set forth in a) is RP 850. In certain cases, the sequence set forth in a) is RP 851. In certain cases, the sequence set forth in a) is RP 852. In certain cases, the sequence set forth in a) is RP 853.

In certain instances, the sequence set forth in b) has a sequence having at least 80% sequence identity with the sequence defined in a). In certain instances, the sequence set forth in b) has a sequence having at least 85% sequence identity with the sequence defined in a). In certain instances, the sequence set forth in b) has a sequence having at least 90% sequence identity with the sequence defined in a). In certain instances, the sequence set forth in b) has a sequence having at least 95% sequence identity with the sequence defined in a).

In certain embodiments, the sequence set forth in c) has one or two amino acid substitutions relative to the sequence defined in a), wherein the one or two amino acid substitutions are similar amino acid substitutions according to Table 2. In certain embodiments, the sequence set forth in c) has one or two amino acid substitutions relative to the sequence defined in a), wherein the one or two amino acid substitutions are conservative amino acid substitutions according to Table 2. In certain embodiments, the sequence set forth in c) has one or two amino acid substitutions relative to the sequence defined in a), wherein the one or two amino acid substitutions are highly conservative amino acid substitutions according to Table 2. Any of the variations of immunomodulatory peptides descried herein may be applied to the parent peptides of Table 3.

Excluded Polypeptides

Compositions of the present disclosure optionally exclude polypeptides described in US Patent Application Nos. 2012/0270770 and 2003/0109452, and U.S. Pat. No. 6,559,281, the disclosures of which are herein incorporated by reference in their entirety. Accordingly, one or more polypeptides and/or uses of such polypeptides described in such publications can be excluded from the scope of the presently disclosed composition and/or methods. Moreover, any of the polypeptides disclosed in Tables 3-9 of WO2016/061133 by Jaynes et al., the disclosure of which tables is herein incorporated by reference, can be optionally excluded from the compositions disclosed herein and/or methods of using such compounds. In some cases, any of the polypeptides disclosed in instant Table 4 can be optionally excluded from compositions disclosed herein and/or methods of using such compounds.

In some cases, the immunomodulatory peptide of the formulae described herein is NOT a polypeptide of Table 4.

TABLE 4

| RP# | SEQ ID NO: | Sequence |
|---|---|---|
| 182 | 20 | KFRKAFKRFF |
| 183 | 21 | FFRKFAKRFK |
| 185 | 22 | FFKKFFKKFK |
| 186 | 23 | KFKKFFKKFF |
| 233 | 24 | KFKKAFKKAF |

Modified Polypeptides

Embodiments of the present disclosure include the modification of any of the immunomodulatory polypeptides of the present disclosure, by chemical or genetic means. Examples of such modification include construction of peptides of partial or complete sequence with non-natural amino acids and/or natural amino acids in L or D forms. For example, any of the peptides disclosed herein and any variants thereof could be produced in an all-D form. Furthermore, polypeptides of the present disclosure can be modified to contain carbohydrate or lipid moieties, such as sugars or fatty acids, covalently linked to the side chains or the N- or C-termini of the amino acids. In addition, the polypeptides of the present disclosure can be modified to enhance solubility and/or half-life upon being administered. For example, polyethylene glycol (PEG) and related polymers have been used to enhance solubility and the half-life of protein therapeutics in the blood. Accordingly, the polypeptides of the present disclosure can be modified by PEG polymers and the like. Polypeptides of the present disclosure can also be modified to contain sulfur, phosphorous, halogens, metals, etc. And amino acid mimics can be used to produce polypeptides of the present disclosure (e.g., having a structure based on the Structural Algorithm or a structure similar to any of the immunomodulatory polypeptides disclosed herein). In certain embodiments, polypeptides of the present disclosure that include amino acid mimics have enhanced properties, such as resistance to degradation. For example, polypeptides of the present disclosure can include one or more (e.g., all) peptoid monomers.

Immunomodulatory polypeptides can be linked to another molecule via a biodegradable linkage, such as a disulfide bond. The disulfide bond can be mediated by the sulfhydryl group of a cysteine residue found in the immunomodulatory polypeptide and a sulfhydryl group in the other molecule. The cysteine residue can be, e.g., located at either the C-terminal or N-terminal end of immunomodulatory polypeptide. Using a disulfide linkage of this sort, polypeptides of the present disclosure can be conveniently linked to various types of useful molecules. For example, the linkage can be with another immunomodulatory polypeptide (which optionally includes a C-terminal or N-terminal cysteine residue), a fluorescent label (e.g., Dylight 350), a chemotherapeutic agent (e.g., a taxol derivative formed by adding a sulfhydral group to an appropriate site on the taxol ring structure, followed by oxidation with a cysteine-containing peptide of the present disclosure), or the like.

Linked immunomodulatory polypeptides (e.g., homo- or heterodimers) can bind to a target molecule (e.g., a target protein, such as a pro-inflammatory signaling protein) with a binding energy that is greater than that of either monomer polypeptide alone. Thus, for example, the energy of binding of linked immunomodulatory polypeptides to an NF-kB Class II protein (e.g., RelB) can be at least −700 kcal/mol, and in certain embodiments at least −750, −800, −900, −1000, −1100, −1200, −1250, −1300, −1350, −1400, −1425, −1450, −1475, −1500, −1525, −1550, −1575, −1600 kcal/mol, or greater. The energy of binding can be determined, e.g., in silico, in vitro, or in vivo, using methods well-known in the art (e.g., using the ClusPro™ algorithm).

In some instances, where the modified peptide is covalently linked to a molecule of interest, the resulting compound can be termed a peptide conjugate. Any convenient molecules of interest may be attached to the subject immunomodulatory peptides. The molecule of interest may be peptidic or non-peptidic, naturally occurring or synthetic. Molecules of interest suitable for use in conjunction with the subject immunomodulatory peptides include, but are not limited to, a protein domain, a polypeptide, a peptide tag, a specific binding moiety (e.g., an antibody or antibody fragment), a polymeric moiety such as a polyethylene glycol (PEG), a carbohydrate, a dextran or a polyacrylate, a linker, a moiety that imparts desirable drug-like properties such as a half-life extending moiety, a label and a solid support. In some cases, the molecule of interest may confer on the resulting modified peptides enhanced and/or modified properties and functions including, but not limited to, increased water solubility, ease of chemical synthesis, cost, bioconjugation site, stability, pI, aggregation, reduced non-specific binding and/or specific binding to a second target protein, e.g., as described herein.

In some embodiments of any one of the peptide sequences described herein, the peptide sequence may be extended to include one or more additional residues at the N-terminal and/or C-terminal of the sequence, such as two or more, three or more, four or more, five or more, 6 or more, or even more additional residues. Any convenient residues may be included at the N-terminal and/or C-terminal of the peptide to provide for a desirable property or group, such as increased solubility via a water soluble group, a linkage for dimerization or multimerization, a linkage for connecting to a label or a specific binding moiety.

In some cases, the subject modified peptide is described by formula:

where B is an immunomodulatory peptide (e.g., as described herein); L is an optional linking group; and M is a molecule of interest, where L is attached to B at any convenient location (e.g., the N-terminal, C-terminal or via the sidechain of a residue not involved in binding to the target).

The modified peptides may include one or more molecules of interest. In some instances, the molecule of interest is covalently attached via the alpha-amino group of the N-terminal residue, or is covalently attached to the alpha-carboxyl acid group of the C-terminal residue.

The molecules of interest may include a polypeptide or a protein domain. Polypeptides and protein domains of interest include, but are not limited to: gD tags, c-Myc epitopes, FLAG tags, His tags, fluorescence proteins (e.g., GFP), beta-galactosidase protein, GST, albumins, immunoglobulins, antibodies, Fc domains, or similar antibody-like fragments, leucine zipper motifs, a coiled coil domain, a hydrophobic region, a hydrophilic region, a polypeptide comprising a free thiol which forms an intermolecular disulfide bond between two or more multimerization domains, a "protuberance-into-cavity" domain, beta-lactoglobulin, or fragments thereof.

The molecules of interest may include a half-life extending moiety. The term "half-life extending moiety" refers to a pharmaceutically acceptable moiety, domain, or "vehicle" covalently linked or conjugated to the subject compound, that prevents or mitigates in vivo proteolytic degradation or other activity-diminishing chemical modification of the subject compound, increases half-life or other pharmacokinetic properties (e.g., rate of absorption), reduces toxicity, improves solubility, increases biological activity and/or target selectivity of the subject compound with respect to a target of interest, increases manufacturability, and/or reduces immunogenicity of the subject compound, compared to an unconjugated form of the subject compound.

In certain embodiments, the half-life extending moiety is a polypeptide that binds a serum protein, such as an immunoglobulin (e.g., IgG) or a serum albumin (e.g., human serum albumin (HSA)). Polyethylene glycol is an example of a useful half-life extending moiety. Exemplary half-life extending moieties include a polyalkylene glycol moiety (e.g., PEG), a serum albumin or a fragment thereof, a transferrin receptor or a transferrin-binding portion thereof, and a moiety comprising a binding site for a polypeptide that enhances half-life in vivo, a copolymer of ethylene glycol, a copolymer of propylene glycol, a carboxymethylcellulose, a polyvinyl pyrrolidone, a poly-1,3-dioxolane, a poly-1,3,6-trioxane, an ethylene/maleic anhydride copolymer, a polyaminoacid (e.g., polylysine), a dextran n-vinyl pyrrolidone, a poly n-vinyl pyrrolidone, a propylene glycol homopolymer, a propylene oxide polymer, an ethylene oxide polymer, a polyoxyethylated polyol, a polyvinyl alcohol, a linear or branched glycosylated chain, a polysialic acid, a polyacetal, a lipid, a long chain fatty acid, a long chain hydrophobic aliphatic group, an immunoglobulin Fc domain (see, e.g., U.S. Pat. No. 6,660,843), an albumin (e.g., human serum albumin; see, e.g., U.S. Pat. No. 6,926,898 and US 2005/0054051; U.S. Pat. No. 6,887,470), a transthyretin (TTR; see, e.g., US 2003/0195154; 2003/0191056), or a thyroxine-binding globulin (TBG).

In certain embodiments, the half-life extending moiety is a lipid. In certain embodiments, the half-life extending moiety is a fatty acid. Any convenient lipids and fatty acids may be used in the subject modified compounds. See e.g., Chae et al., "The fatty acid conjugated exendin-4 analogs for type 2 antidiabetic therapeutics", J. Control Release. 2010 May 21; 144(1):10-6.

In certain embodiments, the immunomodulatory peptide is modified to include a specific binding moiety. The specific binding moiety is a moiety that is capable of specifically binding to a second moiety that is complementary to it. In some cases, the specific binding moiety binds to the complementary second moiety with an affinity of at least $10^{-7}$ M (e.g., as measured by a $K_D$ of 100 nM or less, such as 30 nM or less, 10 nM or less, 3 nM or less, 1 nM or less, 300 pM or less, or 100 pM or even less). Complementary binding moiety pairs of specific binding moieties include, but are not limited to, a ligand or activator/promoter and a receptor, an antibody and an antigen, complementary polynucleotides, complementary protein homo- or heterodimers, an aptamer and a small molecule, and a polyhistidine tag and nickel. The specific binding pairs may include analogs, derivatives and fragments of the original specific binding member. For example, an antibody directed to a protein antigen may also recognize peptide fragments, chemically synthesized, labeled protein, derivatized protein, etc. so long as an epitope is present. Protein domains of interest that find use as specific binding moieties include, but are not limited to, Fc domains, or similar antibody-like fragments, leucine zipper motifs, a coiled coil domain, a hydrophobic region, a hydrophilic region, a polypeptide comprising a free thiol which forms an intermolecular disulfide bond between two or more multimerization domains, or a "protuberance-into-cavity" domain (see e.g., WO 94/10308; U.S. Pat. No. 5,731,168, Lovejoy et al. (1993), Science 259: 1288-1293; Harbury et al. (1993), Science 262: 1401-05; Harbury et al. (1994), Nature 371:80-83; Hakansson et al. (1999), Structure 7: 255-64.

In certain embodiments, the peptide is a linked specific binding moiety that specifically binds a target protein. The linked specific binding moiety can be an antibody, an antibody fragment, a receptor activator, or an aptamer. The linked specific binding moiety can specifically bind any convenient target protein, e.g., a target protein that is desirable to target in conjunction with the subject methods of treatment. Target proteins of interest include, but are not limited to, PDGF (e.g., PDGF-B), VEGF-B, VEGF-C, VEGF-D, EGF, EGFR, Her2, PD-1, PD-L1, OX-40 and LAG3. In certain embodiments, the linked specific binding moiety is a receptor activator or ligand, e.g., a protein ligand associated with an inflammatory pathway, such as interleukin 13 (IL-13) or a molecule that activates is a member of the toll-like receptor (TLR) family, e.g., TLR3. In certain instances, the linked specific binding moiety (e.g., a protein, antibody, or antibody fragment) can be further linked to an additional active agent (e.g., a chemotherapeutic agent, e.g., as described herein).

An immunomodulatory polypeptide (e.g., as described herein) may be conjugated to an additional active agent to provide a conjugate of an immunomodulatory polypeptide. Once the subject peptides have been generated and/or fabricated and selected according to the teachings herein they may be linked with, fused to, conjugated to (e.g., covalently or non-covalently) or otherwise associated with pharmaceutically active or diagnostic moieties or biocompatible modifiers. The term "peptide conjugate" refers to any biologically active or detectable molecule or drug associated with the disclosed immunomodulatory peptide compound regardless of the method of association. In this respect it will be understood that such conjugates may, in addition to the disclosed immunomodulatory peptides, comprise peptides, polypeptides, proteins, prodrugs which are metabolized to an active agent in vivo, polymers, nucleic acid molecules, small molecules, binding agents, mimetic agents, synthetic drugs, inorganic molecules, organic molecules and radioisotopes. Moreover, as indicated above the selected conjugate may be covalently or non-covalently associated with, or linked to, the subject peptide and exhibit various stoichiometric molar ratios depending, at least in part, on the method used to effect the conjugation.

In certain instances, the molecule of interest is a second active agent, e.g., an active agent or drug that finds use in conjunction with targets of interest in the subject methods of treatment. In certain instances, the molecule of interest is a small molecule, a chemotherapeutic, an antibody, an antibody fragment, a bispecific antibody, an aptamer, or a L-protein. In some embodiments, the peptide is modified to include a moiety that is useful as a pharmaceutical (e.g., a protein, nucleic acid, organic small molecule, etc.). Exemplary pharmaceutical proteins include, e.g., cytokines, antibodies, chemokines, growth factors, interleukins, cell-surface proteins, extracellular domains, cell surface receptors, cytotoxins, etc. Exemplary small molecule pharmaceuticals include small molecule toxins or therapeutic agents. Any convenient therapeutic or diagnostic agent (e.g., as described herein) can be conjugated to an immunomodulatory peptide. A variety of therapeutic agents including, but not limited to, anti-cancer agents, antiproliferative agents, cytotoxic agents and chemotherapeutic agents are described below in the section entitled Combination Therapies, any one of which can be adapted for use in the subject peptide conjugates.

In certain embodiments, the modified peptide may be conjugated to a bispecific antibody, e.g., an engineered bispecific monoclonal antibody that can simultaneously bind to two different types of antigen of interest.

In certain embodiments, the modified peptide may include a cell penetrating peptide (e.g., tat). The cell penetrating peptide may facilitate cellular uptake of the molecule. Any convenient tag polypeptides and their respective antibodies may be used. Examples include poly-histidine (poly-his) or poly-histidine-glycine (poly-his-gly) tags; the flu HA tag polypeptide and its antibody 12CA5 [Field et al., Mol. Cell. Biol. 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology 6:1204-1210 (1988)]; the KT3 epitope peptide [Martin et al., Science 255:192-194 (1992)]; tubulin epitope peptide [Skinner et al., J. Biol. Chem. 266:15163-15166 (1991)]; and the T7 gene 10 protein peptide tag [Lutz-Freyermuth et al., Proc. Natl. Acad. Sci. U.S.A. 87:6393-6397 (1990)].

Those skilled in the art will appreciate that a number of different reactions are available for the attachment or association of therapeutic or diagnostic moieties and/or linkers to the subject immunomodulatory peptides. In certain embodiments, this may be accomplished by reaction of the amino acid residues of the peptide, e.g., as described herein, including the amino terminal, the C-terminal carboxylic acid, the amine groups of lysine, the free carboxylic acid groups of glutamic and aspartic acid, the sulfhydryl groups of cysteine and the various moieties of the aromatic amino acids. One method of covalent attachment is the carbodiimide reaction to link a carboxy (or amino) group of a compound to amino (or carboxy) groups of the subject peptide. Additionally, bifunctional agents such as dialdehydes or imidoesters have been used to link the amino group of a subject peptide to amino groups of an antibody molecule. Also available for attachment of drugs to immunomodulatory peptides is maleimide—thiol conjugation chemistry, Click chemistry, e.g., between an azido and an alkynyl group, and the like. Also available for attachment of drugs to peptides is the Schiff base reaction. This method can involve the periodate oxidation of a drug that contains glycol or hydroxy groups, thus forming an aldehyde which is then reacted with the binding agent. Attachment occurs via formation of a Schiff base with amino groups of the binding agent. Isothiocyanates and azlactones can also be used as coupling agents for covalently attaching drugs to binding agents.

It will be appreciated that several varieties or types of linker may be used to associate the disclosed immunomodulatory peptides with pharmaceutically active or diagnostic moieties or biocompatible modifiers. In some embodiments, the linker is cleavable under intracellular conditions, such that cleavage of the linker releases the drug unit from the antibody in the intracellular environment. In certain embodiments, the linker unit is not cleavable. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p 234-242).

Compositions

Compositions of the present disclosure include an immunomodulatory polypeptide that satisfies one of the structural formula described herein. For example, the immunomodulatory polypeptide can have a striapathic region having a sequence that conforms with any one of Formulas disclosed herein. Typically, the immunomodulatory polypeptide included in the compositions of the present disclosure will be a synthetic polypeptide (e.g., made by chemical synthesis and/or produced recombinantly).

The compositions of the present disclosure can include a single immunomodulatory polypeptide, or combinations thereof. The compositions can be substantially free of proteins and other polypeptides that do not satisfy the structural algorithm disclosed herein. As used herein, the term "substantially free of proteins and other polypeptides" means that less than 5% of the protein content of the composition is made up of proteins and other polypeptides that are not an immunomodulatory polypeptide of the present disclosure. A composition that is substantially free of non-immunomodulatory polypeptides of the present disclosure can have less than 4%, 3%, 2%, 1%, 0.5%, 0.1%, 0.05%, 0.01%, or less of proteins or other polypeptides that do not satisfy the structural algorithm disclosed herein. Thus, the compositions can be substantially free of blood proteins, such as serum albumin, globulins, fibrinogen, and clotting factors. Alternatively, the compositions can be substantially free of globulins, fibrinogen, and clotting factors, but can include purified or recombinantly produced serum albumin.

The compositions of the present disclosure in certain embodiments contain an immunomodulatory polypeptide that is not naturally found in a human or other mammal or animal. However, compositions of the present disclosure can include an immunomodulatory polypeptide that is naturally found in a human or other mammal or animal, provided that the composition is substantially free of biological molecules (such as non-immunomodulatory polypeptides, nucleic acids, lipids, carbohydrates, and metabolites) that are associated with the immunomodulatory polypeptide in vivo or co-purify with the immunomodulatory polypeptide. As used herein, the term "substantially free of biological molecules" means that less than 5% of the dry weight of the composition is made up of biological molecules that are not immunomodulatory polypeptides. A composition that is substantially free of such biological molecules can have less than 4%, 3%, 2%, 1%, 0.5%, 0.1%, 0.05%, 0.01%, or less of biological molecules that are not immunomodulatory polypeptides. Thus, for example, the composition can be substantially free of biological molecules that are abundant in the blood, such the proteins discussed above, fatty acids, cholesterol, non-protein clotting factors, metabolites, and the like. In addition, the composition can be substantially free of cells, including red blood cells, white blood cells, and platelets, and cell fragments.

The compositions of the present disclosure can include at least 1 mg (e.g., at least 5, 10, 20, 30, 40, 50, 75, 100, 150, 200, 250, 300, 400, 500, 600, 700, 800, 900, 1000 mg, or more) of immunomodulatory polypeptide. Thus, for example, the compositions can include an amount of immunomodulatory polypeptide equal to about 1 mg to about 1000 mg (e.g., about 5 mg to about 900 mg, about 5 mg to about 800 mg, about 5 mg to about 700 mg, about 5 mg to about 600 mg, about 10 mg to about 500 mg, about 10 mg to about 400 mg, about 10 mg to about 300 mg, about 10 mg to about 250 mg, about 10 mg to about 200 mg, about 10 mg to about 150 mg, about 10 mg to about 100 mg, about 50 mg to about 500 mg, about 50 mg to about 400 mg, about 50 mg to about 300 mg, about 50 mg to about 250 mg, about 50 mg to about 200 mg, about 50 mg to about 150 mg, about 50 mg to about 100 mg, about 75 mg to about 500 mg, about 75 mg to about 400 mg, about 75 mg to about 300 mg, about 75 mg to about 250 mg, about 75 mg to about 200 mg, about 75 mg to about 150 mg, about 75 mg to about 100 mg, about 100 mg to about 500 mg, about 100 mg to about 400 mg, about 100 mg to about 300 mg, about 100 mg to about 250 mg, about 100 mg to about 200 mg, or any other range containing two of the foregoing endpoints).

The compositions of the present disclosure can include a solution that contains at least 1 mg/ml (e.g., at least 5, 10, 15, 20, 25, 30, 35, 40, 45, 50, 55, 60, 65, 70, 75, 80, 85, 90, 95, 100 mg/ml or more) of an immunomodulatory polypeptide. Thus, for example, the compositions can include a solution having an immunomodulatory polypeptide concentration of about 1 mg/ml to about 1000 mg/ml (e.g., about 5 mg/ml to about 900 mg/ml, about 5 mg/ml to about 800 mg/ml, about 5 mg/ml to about 700 mg/ml, about 5 mg/ml to about 600 mg/ml, about 5 mg/ml to about 500 mg/ml, about 10 mg/ml to about 500 mg/ml, about 10 mg/ml to about 400 mg/ml, about 10 mg/ml to about 300 mg/ml, about 10 mg/ml to about 250 mg/ml, about 10 mg/ml to about 200 mg/ml, about 10 mg/ml to about 150 mg/ml, about 10 mg/ml to about 100 mg/ml, about 50 mg/ml to about 500 mg/ml, about 50 mg/ml to about 400 mg/ml, about 50 mg/ml to about 300 mg/ml, about 50 mg/ml to about 250 mg/ml, about 50 mg/ml to about 200 mg/ml, about 50 mg/ml to about 150 mg/ml, about 50 mg/ml to about 100 mg/ml, about 75 mg/ml to about 500 mg/ml, about 75 mg/ml to about 400 mg/ml, about 75 mg/ml to about 300 mg/ml, about 75 mg/ml to about 250 mg/ml, about 75 mg/ml to about 200 mg/ml, about 75 mg/ml to about 150 mg/ml, about 75 mg/ml to about 100 mg/ml, about 100 mg/ml to about 500 mg/ml, about 100 mg/ml to about 400 mg/ml, about 100 mg/ml to about 300 mg/ml, about 100 mg/ml to about 250 mg/ml, about 100 mg/ml to about 200 mg/ml, about 10 mg/ml to about 150 mg/ml, or any other range containing two of the foregoing endpoints).

The compositions of the present disclosure include pharmaceutical compositions. Such pharmaceutical compositions can comprise one or more immunomodulatory polypeptides and a pharmaceutically acceptable carrier. Pharmaceutical compositions can further include a protein other than an immunomodulatory polypeptide of the present disclosure and/or a chemotherapeutic agent. The other protein can be a therapeutic agent, such as a therapeutic antibody. The therapeutic protein or antibody can have immunomodulatory properties or other properties that the immunomodulatory polypeptides of the present disclosure augment or are augmented by. Alternatively, the other protein can be a carrier protein, such as serum albumin (e.g., HSA). The serum albumin (e.g., HAS, BSA, etc.) can be purified or recombinantly produced. By mixing the immunomodulatory polypeptide(s) in the pharmaceutical composition with serum album, the immunomodulatory polypeptides can be effectively "loaded" onto the serum albumin, allowing a greater amount of immunomodulatory polypeptide to be successfully delivered to a site of inflammation. The chemotherapeutic agent can be, for example, an anti-cancer chemotherapeutic agent. Such chemotherapeutic agents include, but are not limited to, Gemcitabine, Docetaxel, Bleomycin, Erlotinib, Gefitinib, Lapatinib, Imatinib, Dasatinib, Nilotinib, Bosutinib, Crizotinib, Ceritinib, Trametinib, Bevacizumab, Sunitinib, Sorafenib, Trastuzumab, Ado-trastuzumab emtansine, Rituximab, Ipilimumab, Rapamycin, Temsirolimus, Everolimus, Methotrexate, Doxorubicin, Abraxane, Folfirinox, Cisplatin, Carboplatin, 5-fluorouracil, Teysumo, Paclitaxel, Prednisone, Levothyroxine, and Pemetrexed.

In some instances of the subject pharmaceutical compositions, the composition includes an immunomodulatory polypeptide that is a CD206-binding peptide (e.g., as described herein) and a chemotherapeutic agent. In some embodiments, the immunomodulatory polypeptide that finds use in a combination composition is a peptide of Table 3. In certain instances, the immunomodulatory peptide (e.g., a peptide of Table 3) is combined with a chemotherapeutic agent. In certain cases of the pharmaceutical composition, the chemotherapeutic agent is Gemcitabine. In some cases of the pharmaceutical composition, the chemotherapeutic agent is Docetaxel. In some cases of the pharmaceutical composition, the chemotherapeutic agent is Abraxane.

In some instances of the subject pharmaceutical compositions, the composition includes an immunomodulatory polypeptide that is a CD206-binding peptide (e.g., as described herein) and is conjugated to a second additional agent (e.g., as described herein). In some cases, the additional agent is a chemotherapeutic agent. In some embodiments, the immunomodulatory polypeptide that finds use in the subject peptide conjugate is a peptide of Table 3. In certain instances, the immunomodulatory peptide (e.g., a peptide of Table 3) is conjugated to a chemotherapeutic agent. In certain cases of the subject peptide conjugates, the chemotherapeutic agent is Gemcitabine. In some cases of the subject peptide conjugates, the chemotherapeutic agent is Docetaxel. In some cases of the subject peptide conjugates, the chemotherapeutic agent is Abraxane. In some cases of the subject peptide conjugates, the chemotherapeutic agent is paclitaxel.

In some cases, a subject pharmaceutical composition that finds use in the treatment of cancer, e.g., ovarian cancer, includes an immunomodulatory polypeptide in combination with a vaccination therapy, e.g., a dendritic cell (DC) vaccination agent that promotes Th1/Th17 immunity. In some cases of the pharmaceutical composition, the immunomodulatory polypeptide is an adjuvant in combination with a Th17-inducing vaccination agent.

The pharmaceutical compositions of the present invention can be formulated for oral administration, parenteral administration, inhalation administration, topical administration, mucosal administration, or the like. In some embodiments, the administering is via a route selected from peroral, intravenous, intraperitoneal, inhalation, intranasal, intraprostatic, and intratumoral. The present invention is not limited by the route of administration. Compositions formulated for oral delivery can, for example, include an enteric coat, to ensure that peptides contained therein reach the intestine and beyond. Enteric formulations such as gastro resistant capsules for oral administration, suppositories for rectal or vaginal administration also form part of this disclosure. Compositions formulated for topical delivery can be, for example, suspended in a gel or cream, coated on a microneedle, or infused into a bandage or topical patch, to extend the duration of action of the peptides contained therein. Any inhalable formulation which can provide for an aerosolized form including a subject peptide for delivery to a patient via the intrapulmonary route may be used in conjunction with the present disclosure. In some cases, the subject compositions are administered by intratumoral injection, e.g., into injectable cutaneous, subcutaneous, and/or nodal tumors.

In some embodiments, compositions are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal, and rectal techniques), as well as European Publication No. 517,565 and Illum et al., J. Controlled Rel., 1994, 29:133-141 (e.g., for techniques of intranasal administration). In some cases, the compositions of the present invention may be administered dermally or transdermally using standard techniques. Methods of intranasal vaccination include the administration of a droplet or spray form of the subject composition into the nasopharynx of a subject to be treated. In some embodiments, a nebulized or aerosolized composition is provided.

Also provided are liposomal pharmaceutical compositions comprising the subject immunomodulatory peptides. Any convenient nanocarriers and liposomes can be adapted for use in preparing liposomal formulations of the subject peptides, such as those nanocarriers and liposomes described by Arias in "Liposomes in drug delivery: a patent review". Expert Opinion on Therapeutic Patents, 23, 2013, issue 11, p. 1399-1414; and Torchilin in "Multifunctional nanocarriers", Advanced Drug Delivery Reviews, Volume 58, Issue 14, 1 Dec. 2006, Pages 1532-1555.

Also provided are nanoparticle formulations or compositions including the subject immunomodulatory peptides. Nanopaticle formulations or compositions can increase the aqueous solubility of a peptide of interest and can achieve protected, sustained, and targeted delivery of the peptide in therapeutic applications (e.g., as described herein). In some cases, the formulation is a polymer-based nanoparticle formulation. Nanopaticle formulations of interest include albumin nanoparticles, e.g., human serum albumin containing nanoparticle formualtions. In some cases, a desolvation technique can be used for the preparation of albumin nanoparticles. Particle size, peptide drug release, encapsulation efficiency and peptide drug polymer interactions can be determined and selected using any convenient in vitro methods. Cell culture studies, in vivo pharmacokinetics, e.g., in rats, can be used for biological characterization of a desirable formulation.

In some instances, the nanoparticle formulation compositions including the subject immunomodulatory peptides is composed of iron oxide nanoparticles (IONPs). IONPs find use in a variety of biomedical applications. In some cases, an IONP formulation can exhibit high uptake in macrophages and/or target cancer cells. IONPs having a desirable cytotoxicity, in vivo distribution, and/or clearance can be selected for use in conjunction with the subject immunomodulatory peptides. A variety of well-characterized IONPs with different sizes and coatings can be utilized in the subject compositions and formulations. In some cases, polyethylenimine (PEI)-coated IONPs or PEGylated IONPs are utilized. IONPs can enhance cytotoxicity of the subject formulation through multiple mechanisms such as ROS production and apoptosis.

Also provided are kits including an immunomodulatory polypeptide that is a CD206-binding peptide (e.g., as described herein) and an additional agent (e.g., a chemotherapeutic agent or an immunotherapeutic agent) for use in treating cancer. The kit can include a dose of an immunomodulatory peptide in an amount effective to inhibit proliferation of cancer cells in a subject. The kit can also include a dose of an additional agent, such as a chemotherapeutic agent or an immunotherapeutic agent (e.g., as described herein) in an amount effective to inhibit proliferation of cancer cells in a subject. The kit in some cases includes an insert with instructions for administration of the immunomodulatory peptide and/or the additional agent (e.g., a chemotherapeutic agent or an immunotherapeutic agent). In some instances, the set of instructions for the combination therapy may recommend (i) a lower dose of the immunomodulatory peptide, when used in combination with the chemotherapeutic agent, (ii) a lower dose of the additional agent (e.g., a chemotherapeutic agent or an immunotherapeutic agent), when used in combination with the immunomodulatory peptide, and/or (iii) a different dosing regimen for one or both agent than would normally be recommended.

Methods

This disclosure provides methods of modulating macrophage activity using an immunomodulatory peptide (e.g., as described herein). In some cases of the method, the macrophage activity that is modulated is macrophage polarization. The method can include contacting a macrophage with a CD206-binding agent that is a peptide of this disclosure to modulate activity of the macrophage. In some cases, by modulating activity is meant inhibition of macrophage activity. The subject method can provide for reduction of the viability of the macrophage, which viability can be determined using any convenient methods.

In certain embodiments, an immunomodulatory polypeptide of this disclosure can bind to human CD206 with an affinity of at least −650 kcal/mol, and in certain embodiments at least −700, −750, −800, −850, −900, −925, −950, −975, −1000, −1025, −1050 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

The macrophage targeted using the subject method can be a M2 macrophage or a tumor associated macrophage (TAM). The macrophage that is targeted can be in vitro or in vivo.

In certain embodiments, a peptide of this disclosure binds to two or more targets (e.g., pro-inflammatory targets). In some embodiments, a variant polypeptide binds to three, four, five, or more pro-inflammatory targets. For example, a variant polypeptide can bind to any combination of targets disclosed herein (e.g., an NF-kB Class II protein and human serum albumin (HSA)), as discussed below. Such binding can be based on in silico, in vitro, or in vivo data.

Exemplary RP peptides of interest can interact with various signaling molecules associated with inflammation, including NF-kB Class II subunit RelB, TGFβ, Notch1, Wnt8R, TRAIL, IL6R, IL10R, EGFR, and CDK6, as well as other membrane associated signaling molecules, including CD206, CD47 and SIRP-α, translational modification protein transglutaminase 2 (TGM2), and histone modification enzyme histone methyl transferase (HMT). In certain cases, the subject peptides are CD206-binding peptides. Upon folding of these protein targets to their normal 3-dimensional conformations, an amphipathic cleft is often generated that has high affinity for the immune-modulating peptides herein described.

Further details of the target signaling molecules to which the subject immunomodulatory peptides specifically bind are set forth in WO2016/061133 by Jaynes et al., the disclosure of which is incorporated herein in its entirety.

An immunomodulatory polypeptide that finds use in the subject methods can be based on its ability to bind to the mannose-binding site on CD206 and/or interfere with or block the binding of SIRP-mannose to CD206. For example, the immunomodulatory polypeptide can bind to at least one amino acid residue of CD206 selected from the group consisting of Glu-725, Tyr-729, Glu-733, Asn-747, and Asp-748, or the equivalent amino acid residue(s) in a CD206 protein of another species. Alternatively, the immunomodulatory polypeptide can bind to at least one amino acid residue of human CD206 selected from the group consisting of Phe-708, Thr-709, Trp-710, Pro-714. Glu-719, Asn-720, Trp-721, Ala-722, Glu-725, Tyr-729, Glu-733, Asn-747, Asp-748, Ser-1691, Cys-1693, Phe-1694, and Phe-1703, or the equivalent amino acid residue(s) in a CD206 protein of another species. In certain embodiments, the immunomodulatory polypeptide can bind to at least one amino acid residue of CD206 selected from the group consisting of Phe-708, Trp-710, Trp-721, Glu-725, Tyr-729, Glu-733, or the equivalent amino acid residue(s) in a CD206 protein of another species.

In certain instances, an immunomodulatory polypeptide binds a fibronectin (FBN) domain of CD206 and/or interfere with or block the binding of collagens to CD206. In some cases, the immunomodulatory polypeptide can specifically bind a fibronectin (FBN) domain of CD206. In some instances, a subject immunomodulatory polypeptide binds a C-type carbohydrate recognition domain (CRD) domain of the CD206 to modulate (e.g., activate) the activity of CD206. In some cases, a subject immunomodulatory polypeptide binds a C-type carbohydrate recognition domain (CRD) domain of the CD206 to modulate (e.g., interfere with, block or inhibit) the activity of CD206. In certain cases, the CRD domain to which a subject immunomodulatory polypeptide specifically binds to modulate the activity of CD206 is a CRD 4 or 5 domain.

In certain embodiments, an immunomodulatory polypeptide binds to two or more targets (e.g., pro-inflammatory targets). In some embodiments, an immunomodulatory polypeptide binds to three, four, five, or more pro-inflammatory targets. For example, an immunomodulatory polypeptide can bind to any combination of targets disclosed herein. Such binding can be based on in silico, in vitro, or in vivo data. Thus, an immunomodulatory polypeptide can bind to two or more NF-kB Class II subunits (e.g., RelB and at least one other NF-kB Class II subunit, such as RelA, cRel, NF-kB1, or NF-kB2). Alternatively (or in addition), an immunomodulatory polypeptide can bind to an NF-kB Class II subunit (e.g., RelB) and at least one other signaling molecule (e.g., at least one signaling molecule selected from the group consisting of TGFβ, Notch1, Wnt8R, TRAIL, IL6R, IL10R, EGFR, CDK6, CD206, CD47, SIRP-α, HMT, and TGM2). For example, an immunomodulatory polypeptide can bind to an NF-kB Class II subunit (e.g., RelB) and at least one signaling molecule selected from the group consisting of TGFβ, Notch1, Wnt8R, TRAIL, IL6R, IL10R, EGFR, and CDK6. Alternatively, an immunomodulatory polypeptide can bind to an NF-kB Class II subunit (e.g., RelB) and at least one signaling molecule selected from the group consisting of CD206, CD47, SIRP-α, and TGM2. In other alternatives, an immunomodulatory polypeptide can bind to an NF-kB Class II subunit (e.g., RelB) and HMT. In other alternatives, an immunomodulatory polypeptide can bind to at least one signaling molecule selected from the group consisting of TGFβ, Notch1, Wnt8R, TRAIL, IL6R, IL10R, EGFR, and CDK6, and at least one signaling molecule selected from the group consisting of CD206, CD47, SIRP-α, and TGM2. In other alternatives, an immunomodulatory polypeptide can bind to at least one signaling molecule selected from the group consisting of TGFβ, Notch1, Wnt8R, TRAIL, IL6R, IL10R, EGFR, and CDK6, and also bind to HMT. In still other embodiments, an immunomodulatory polypeptide can bind to an NF-kB Class II subunit (e.g., RelB), at least one signaling molecule selected from the group consisting of TGFβ, Notch1, Wnt8R, TRAIL, IL6R, IL10R, EGFR, and CDK6, at least one signaling molecule selected from the group consisting of CD206, CD47, SIRP-α, and TGM2, and also HMT. In certain embodiments, an immunomodulatory polypeptide binds to two or more pro-inflammatory targets and also serum albumin (e.g., human serum albumin).

The immunomodulatory polypeptides of the present disclosure provide powerful tools for reducing inflammation and/or treating conditions associated with excessive inflammation (whether acute or chronic). As used herein, the terms "treat," "treating," and similar words shall mean stabilizing, reducing the symptoms of, preventing the occurrence of, or curing a medical condition.

Accordingly, the present disclosure provides methods of reducing the expression level and/or activity of at least one (e.g., 2, 3, 4, 5, or more) pro-inflammatory cytokine(s) at a site of inflammation in a subject. The methods include administering an immunomodulatory polypeptide of the present disclosure (or, for example, a pharmaceutical composition comprising an immunomodulatory polypeptide) to the subject. The pro-inflammatory cytokine can be selected from the group consisting of NF-kB, TNFα, IL-1, IL-6, IL-8, IL-12, IL-17, IL-23, MCP-1, MMP-1, and MMP-9. The reduction can be a reduction of at least 10% (e.g., 15%, 20%, 25%, 30%, 35%, 40%, 45%, 50%, or more) in the expression or activity of the cytokine.

The present disclosure also provides methods of inhibiting an increase in the expression level and/or activity of at least one (e.g., 2, 3, 4, 5, or more) pro-inflammatory cytokine(s) at a potential site of inflammation in a subject. The methods include administering an immunomodulatory polypeptide of the present disclosure (or, for example, a pharmaceutical composition comprising an immunomodulatory polypeptide) to the subject. The pro-inflammatory cytokine can be selected from the group consisting of NF-kB, TNFα, IL-1, IL-6, IL-8, IL-12, IL-17, IL-23, MCP-1, MMP-1, and MMP-9. The methods can inhibit increased cytokine expression and/or activity by limiting such increases to no more than 20% (e.g., 15%, 12.5%, 10%, 7.5%, 5%, 4%, 3%, 2%, 1%, or less).

It is understood that modulation of the level and/or activity of pro-inflammatory cytokine(s) at a site of inflammation in a subject can, in some cases, provide for downstream modulation of the activity of an immune cells of interest (e.g., effector T cells, regulatory T cells (Treg), natural killer cells (NK cells), B cells, and the like) and regulation of a target immune or inflammatory response.

The present disclosure also provides a method of treating or preventing a condition associated with chronic inflammation. The condition associated with chronic inflammation can be irritable bowel disease, ulcerative colitis, colitis, Crohn's disease, idiopathic pulmonary fibrosis, asthma, keratitis, arthritis, osteoarthritis, rheumatoid arthritis, autoimmune diseases, a feline or human immunodeficiency virus (FIV or HIV) infection, cancer, age-related inflammation and/or stem cell dysfunction (e.g., age-related increases in Nlrp3 expression, age-related elevation of SOCS3 in muscle stem cells, etc.), graft-versus-host disease (GVHD), keloids, scleroderma, obesity, diabetes, diabetic wounds, other chronic wounds, atherosclerosis, multiple sclerosis, Parkinson's disease, Alzheimer's disease, macular degeneration, gout, gastric ulcers, gastritis, mucositis, toxoplasmosis, and chronic viral or microbial infections (e.g., such as chronic bacterial or protozoan infections). The methods includes administering an immunomodulatory polypeptide of the present disclosure (or, for example, a pharmaceutical composition comprising an immunomodulatory polypeptide) to a subject suffering from or likely to develop the condition.

The present disclosure also provides methods of treating or preventing fibrosis. The fibrosis can be, for example, pulmonary fibrosis, dermal fibrosis, hepatic fibrosis, renal fibrosis, or fibrosis caused by ionizing radiation. The methods include administering an immunomodulatory polypeptide of the present disclosure (or, for example, a pharmaceutical composition comprising an immunomodulatory polypeptide) to a subject suffering from or likely to develop fibrosis.

The present disclosure also provides methods of treating cancer. The cancer can be colon cancer, breast cancer, leukemia, lymphoma, ovarian cancer, prostate cancer, liver cancer, lung cancer, testicular cancer, cervical cancer, bladder cancer, endometrial cancer, kidney cancer, melanoma, cancers of the thyroid or brain, or ophthalmic cancer. The methods include administering an immunomodulatory polypeptide of the present disclosure (or, for example, a pharmaceutical composition comprising an immunomodulatory polypeptide) to a subject suffering from cancer. The presently disclosed subject matter also provides methods for treating a solid tumor cancer in a subject. In some embodiments, the method comprising administering the subject a therapeutically effective amount of a compound as disclosed herein.

For any of the foregoing methods, the subject can be an animal, such as a domesticated animal (e.g., a horse, cow, pig, goat, sheep, rabbit, chicken, turkey, duck, etc.), a pet (e.g., a dog, cat, rabbit, hamster, gerbil, bird, fish, etc.), a lab animal (e.g., a mouse, rat, monkey, chimpanzee, owl, fish, etc.), a zoo animal (e.g., a gorilla, orangutan, chimpanzee, monkey, elephant, camel, zebra, boar, lion, tiger, giraffe, bear, bird, etc.), a wild animal (e.g., a deer, wolf, mountain lion, bird, etc.), or a human.

In conjunction with any of the foregoing methods, the immunomodulatory polypeptide(s) can be administered at a dose and frequency that depends on the type of animal, the size of the animal, and the condition being treated. Typically, the immunomodulatory polypeptide is administered daily (or every other day, or weekly), in an amount between about 1 mg and about 1000 mg (e.g., about 5 mg to about 900 mg, about 5 mg to about 800 mg, about 5 mg to about 700 mg, about 5 mg to about 600 mg, about 10 mg to about 500 mg, about 10 mg to about 400 mg, about 10 mg to about 300 mg, about 10 mg to about 250 mg, about 10 mg to about 200 mg, about 10 mg to about 150 mg, about 10 mg to about 100 mg, about 50 mg to about 500 mg, about 50 mg to about 400 mg, about 50 mg to about 300 mg, about 50 mg to about 250 mg, about 50 mg to about 200 mg, about 50 mg to about 150 mg, about 50 mg to about 100 mg, about 75 mg to about 500 mg, about 75 mg to about 400 mg, about 75 mg to about 300 mg, about 75 mg to about 250 mg, about 75 mg to about 200 mg, about 75 mg to about 150 mg, about 75 mg to about 100 mg, about 100 mg to about 500 mg, about 100 mg to about 400 mg, about 100 mg to about 300 mg, about 100 mg to about 250 mg, about 100 mg to about 200 mg, or any other range containing two of the foregoing endpoints). The daily dose can be administered once during the day, or broken up into smaller doses that are taken at multiple time points during the day. For a human (and other similarly-sized mammals), a dose of 5 mg/kg every other day can be administered. The immunomodulatory polypeptide can be administered for a fixed period of time (e.g., for 2-3 weeks), at intervals (e.g., administer polypeptide for 2-3 weeks, wait 2-3 weeks, then repeat the cycle), or until such time as the pro-inflammatory cytokine levels have been reduced or stabilized, the chronic inflammatory condition or fibrosis has ameliorated, or the cancer has gone into remission.

The administration of the immunomodulatory polypeptides (or pharmaceutical compositions comprising such polypeptides) in conjunction with any of the foregoing methods can be performed intravenously, intraperitoneally, parenteral, orthotopically, subcutaneously, topically, via inhalation, nasally, orally, sublingually, intraocularly, by means of an implantable depot, using nanoparticle-based delivery systems, microneedle patch, microspheres, beads, osmotic or mechanical pumps, and/or other mechanical means.

In conjunction with any of the foregoing methods, the immunomodulatory polypeptides (e.g., as described herein) (or pharmaceutical compositions comprising such polypeptides) can be administered in combination with another drug designed to reduce or prevent inflammation, treat or prevent chronic inflammation or fibrosis, or treat cancer. In each case, the immunomodulatory polypeptide can be administered prior to, at the same time as, or after the administration of the other drug. For the treatment of cancer, the immunomodulatory polypeptide(s) can be administered in combination with an additional therapeutic agent (e.g., a chemotherapeutic agent or an immumotherapeutic agent) selected from the group consisting of taxanes, nucleoside analogs, steroids, anthracyclines, thyroid hormone replacement drugs, thymidylate-targeted drugs, Chimeric Antigen Receptor/T cell therapies, Chimeric Antigen Receptor/NK cell therapies, apoptosis regulator inhibitors (e.g., B cell CLL/lymphoma 2 (BCL-2) BCL-2-like 1 (BCL-XL) inhibitors), CARP-1/CCAR1 (Cell division cycle and apoptosis regulator 1) inhibitors, colony-stimulating factor-1 receptor (CSF1R) inhibitors, CD47 inhibitors, cancer vaccine (e.g., a Th17-inducing dendritic cell vaccine) and other cell therapies. Specific chemotherapeutic agents include, for example, Gemcitabine, Docetaxel, Bleomycin, Erlotinib, Gefitinib, Lapatinib, Imatinib, Dasatinib, Nilotinib, Bosutinib, Crizotinib, Ceritinib, Trametinib, Bevacizumab, Sunitinib, Sorafenib, Trastuzumab, Ado-trastuzumab emtansine, Rituximab, Ipilimumab, Rapamycin, Temsirolimus, Everolimus, Methotrexate, Doxorubicin, Abraxane, Folfirinox, Cisplatin, Carboplatin, 5-fluorouracil, Teysumo, Paclitaxel, Prednisone, Levothyroxine, Pemetrexed, navitoclax, ABT-199.

In some embodiments, the immunomodulatory polypeptide that finds use in a combination therapy is a peptide having macrophage modulating activity (e.g., as described herein). In certain instances, the immunomodulatory polypeptide is a CD206-binding peptide (e.g., as described herein). In some embodiments, the immunomodulatory polypeptide that finds use in a combination therapy is a peptide of Table 3. In certain instances, the immunomodulatory peptide (e.g., a peptide of Table 3) can be administered in combination with a chemotherapeutic agent to treat cancer. In certain cases, the chemotherapeutic agent is Gemcitabine. In some cases, the chemotherapeutic agent is Docetaxel. In some cases, the chemotherapeutic agent is Abraxane.

For the treatment of cancer (e.g., melanoma, non-small cell lung cancer or a lymphoma such as Hodgkin's lymphoma), the immunomodulatory polypeptide(s) can be administered in combination with an immunotherapeutic agent. An immunotherapeutic agent is any convenient agent that finds use in the treatment of disease by inducing, enhancing, or suppressing an immune response. In some cases, the immunotherapeutic agent is an immune checkpoint inhibitor. Any convenient checkpoint inhibitors can be utilized in combination with the subject peptides, including but not limited to, cytotoxic T-lymphocyte-associated antigen 4 (CTLA-4) inhibitors, programmed death 1 (PD-1) inhibitors and PD-L1 inhibitors. Exemplary checkpoint inhibitors of interest include, but are not limited to, ipilimumab, pembrolizumab and nivolumab. In certain embodiments, for treatment of cancer and/or inflammatory disease, the immunomodulatory polypeptide(s) can be administered in combination with a colony-stimulating factor-1 receptor (CSF1R) inhibitors. CSF1R inhibitors of interest include, but are not limited to, emactuzumab.

Any convenient cancer vaccine therapies and agents can be used in combination with the subject immunomodulatory polypeptide compositions and methods. For treatment of cancer, e.g., ovarian cancer, the immunomodulatory polypeptide(s) can be administered in combination with a vaccination therapy, e.g., a dendritic cell (DC) vaccination agent that promotes Th1/Th17 immunity. Th17 cell infiltration correlates with markedly prolonged overall survival among ovarian cancer patients. In some cases, the immunomodulatory polypeptide finds use as adjuvant treatment in combination with Th17-inducing vaccination.

Also of interest are agents that are CARP-1/CCAR1 (Cell division cycle and apoptosis regulator 1) inhibitors, including but not limited to those described by Rishi et al., Journal of Biomedical Nanotechnology, Volume 11, Number 9, September 2015, pp. 1608-1627(20), and CD47 inhibitors, including, but not limited to, anti-CD47 antibody agents such as Hu5F9-G4.

In certain instances, the combination provides an enhanced effect relative to either component alone; in some cases, the combination provides a supra-additive or synergistic effect relative to the combined or additive effects of the components. A variety of combinations of the subject polypeptides and the chemotherapeutic agent may be employed, used either sequentially or simultaneously. For multiple dosages, the two agents may directly alternate, or two or more doses of one agent may be alternated with a single dose of the other agent, for example. Simultaneous administration of both agents may also be alternated or otherwise interspersed with dosages of the individual agents. In some cases, the time between dosages may be for a period from about 1-6 hours, to about 6-12 hours, to about 12-24 hours, to about 1-2 days, to about 1-2 week or longer following the initiation of treatment.

In some embodiments, the method is a method of reducing cancer cell proliferation, where the method includes contacting the cell with an effective amount of a subject immunomodulatory polypeptide (e.g., as described herein). The method can be performed in combination with a chemotherapeutic agent (e.g., as described herein). The cancer cells can be in vitro or in vivo. In certain instances, the method includes contacting the cell with an immunomodulatory peptide (e.g., a peptide of Table 3) and contacting the cell with a chemotherapeutic agent. Any convenient cancer cells can be targeted. In certain cases, the chemotherapeutic agent is Gemcitabine. In some cases, the chemotherapeutic agent is Docetaxel. In some cases, the chemotherapeutic agent is Abraxane.

Alternatively, for the methods of treating cancer, the immunomodulatory polypeptide(s) (or pharmaceutical compositions comprising such polypeptides) can be administered in combination with radiation therapy. Again, the immunomodulatory polypeptide(s) can be administered prior to, or after the administration of the radiation therapy.

Any of the foregoing methods of the present disclosure further include a step of assessing the efficacy of the therapeutic treatment. Because the immunomodulatory polypeptides of the present disclosure have a demonstrable ability to reduce tissue inflammation and suppress the excessive production of inflammatory mediators such as IL-1, IL-6, IL-12, and TNFα, both in tissues and in serum (data not shown), the efficacy of the therapeutic treatment can be assessed by measuring the levels of such cytokines (e.g., in the serum) to determine whether the levels have responded appropriately to the treatment. Depending on the cytokine levels, the dosage of immunomodulatory polypeptide(s) can be adjusted up or down, as needed.

Definitions

It is to be understood that this invention is not limited to particular embodiments described herein, which as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Examples

Methods and materials of interest that find use in preparing and evaluating the subject immunomodulatory peptides include those disclosed in the experimental section of WO2016/061133 by Jaynes et al., the disclosure of which is incorporated herein in its entirety.

The following examples are put forth so as to provide those of ordinary skill in the art with a complete disclosure and description of how to make and use the present invention, and are not intended to limit the scope of what the inventors regard as their invention, nor are they intended to represent that the experiments below are all or the only experiments performed.

Example 1: Suppression of Tumor Growth

The polypeptides of the present disclosure are also tested for their effect on tumor growth in a mouse model of non-metastatic breast cancer. MCF-7 human non-metastatic breast cancer cells are cultured at 37° C., 5% $CO_2$ in normal growth media. Cells are harvested at 80% to 90% confluence Immune compromised athymic nude mice (J:NU) are divided into 2 groups (9 animals per group). All mice are injected with ~4.5×10$^6$ MCF-7 cells which had been stained with VIVO Tracker 680 and suspended in 200 μl of PBS/Matrigel mixture. Cells are injected subcutaneously on the dorsal surface of treated animals using a 22 gauge needle fitted with a 500 μl syringe.

Animals are designated vehicle and peptide treated. The peptide treated animals are treated with the subject polypeptide. Freshly prepared peptide s dissolved in sterile saline at a concentration of 100 μM and used to treat the animals in the peptide group. Vehicle treated animals are injected with saline buffer alone. All treatments are injected into the tumor mass two times weekly for 5 weeks using a 27½ gauge needle fitted with a 1 ml syringe. Animal weights and tumor volumes are measured 3 times weekly and the fluorescence labeling is followed by VIVO Tracker 680 and IVIS Imaging.

Figure 2:
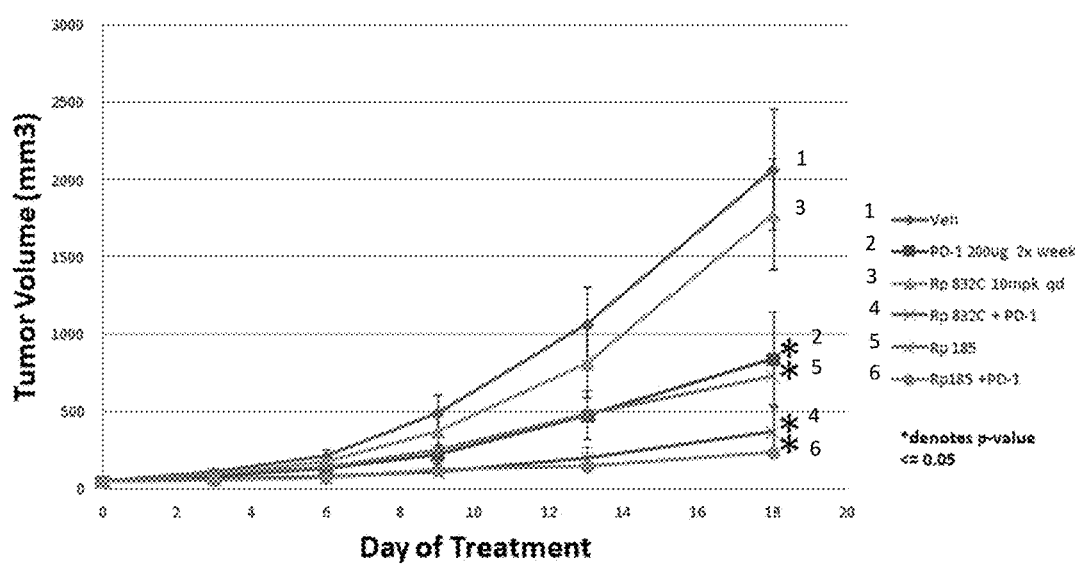
FIG. 2 demonstrates that exemplary peptides of interest synergize with a PD-1 Checkpoint Inhibitor to reduce tumor volume in a mouse tumor inhibition model. Further details are provided in the experimental section below.
Figure 3:
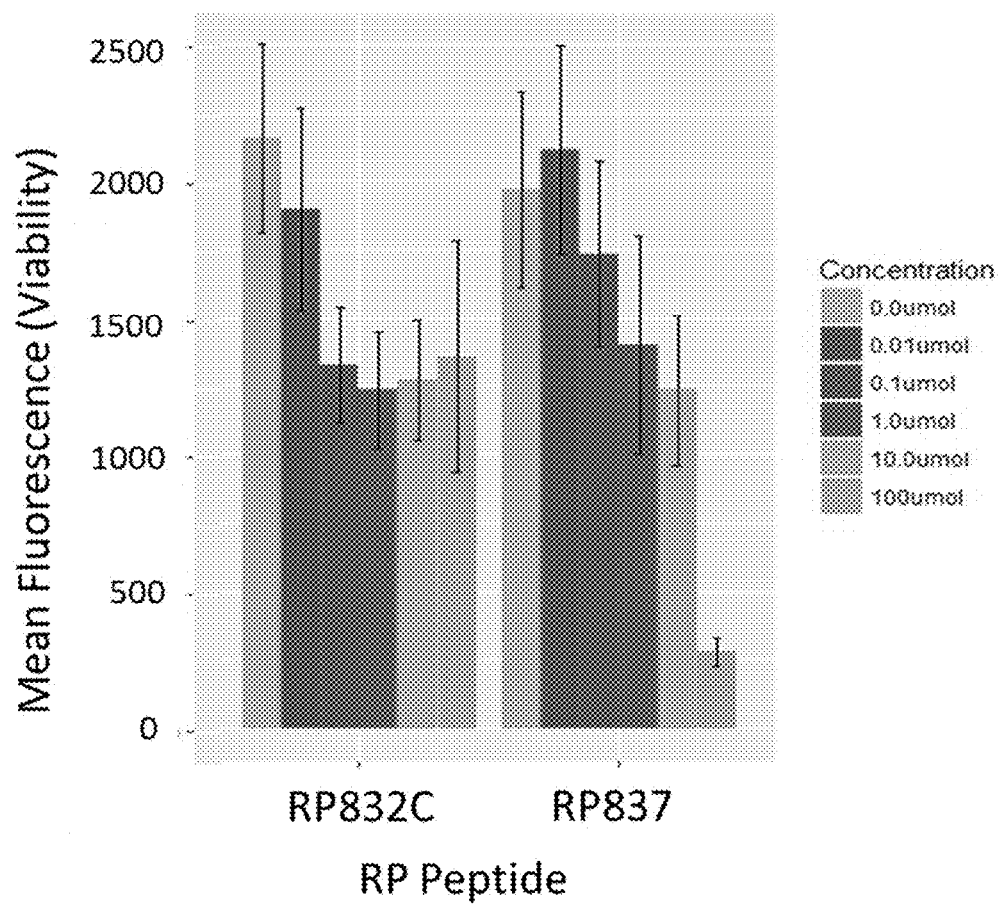
FIG. 3 demonstrates that exemplary peptides RP832C and RP837 reduce viability of macrophages in samples from human scleroderma patients. Macrophage samples were assessed after 96 hours incubation with various concentrations of the peptides.

FIG. 2 shows that peptides RP832C and RP185 reduce tumor volume in a mouse tumor inhibition model. The data demonstrates that polypeptides of the present disclosure suppress tumor growth in vivo.

Example 2: Administering Peptides in Combination with Chemotherapy

Given the significant role of inflammation in tumor genesis and metastasis, as well as the known association of M2 macrophage activity with tumor development, it was anticipated that the administration of peptides of the present disclosure (e.g., selected peptides of Table 3) could positively influence the outcomes of cancer treatment.

To test this theory, cohorts of immunocompromised ("nude") mice are injected with 5×10$^6$ human triple-negative breast cancer cells (MDA-MB-231) under the upper left teat. Following this administration, one cohort receives only vehicle; two of the cohorts receive the chemotherapeutic agent Gemcitabine, at a q4d dose of 40 mg/kg of body weight. One of these cohorts also received test peptide at a daily dose of 5 mg/kg body weight; and a fourth cohort received only peptide at a daily dose of 5 mg/kg body weight. Beginning on day 32 of the study, in the Gemcitabine+RP-182 cohort, concentrations of RP-182 are increased to 20 mg/kg body weight. Tumor volume is assessed at various time points following initial cell administration. After 50 days, the mice are sacrificed.

In a second experiment, xenografts of C42B prostate cancer cells are introduced into four cohorts of mice, and the tumors allowed to grow to approximately 100 m$^3$ before treatment. One cohort is treated only with vehicle; a second with Docetaxel at 2.5 mg/kg body weight administered weekly; a third with test peptide administered daily subcu at 10 mg/kg body weight; and a fourth with both Docetaxel at 2.5 mg/kg weekly and test peptide at 10 mg/kg daily. Tumor volume is assessed at various time points following initial cell administration; after 27 days, the mice are sacrificed.

It is anticipated that the peptides of the present disclosure (e.g., selected peptides of Table 3) will produce synergistic effects when administered with chemotherapeutic agents including Gemcitabine and Docetaxel, as well as checkpoint inhibitor therapies and other immunotherapies. In particular, the peptides of the present disclosure may be particularly useful when used in conjunction with recently-developed CAR-T (chimeric antigen receptor/T cell) therapies. Such therapies, while destroying tumor cells, create a very high systemic burden of dead cell material, overstimulating the immune system and creating a "cytokine storm" which can be fatal to the patient.

Example 3: Investigation of Selected Peptides

Table 5: The binding energies of selected peptides of Tables 3-4 for CD206 were calculated using the ClusPro algorithm:

| RP# | Binding Energy to CD206 in ClusPro |
| --- | --- |
| 832C | −1312 |
| 837 | −1218 |
| 182 | −998 |
| 183 | −943 |
| 107 | −757 |
| 426 | −732 |
| 185 | −953 |
| 186 | −948 |
| 233 | −713 |
| 851 | −714 |
| 852 | −963 |
| 853 | −700 |

Figure 4A:
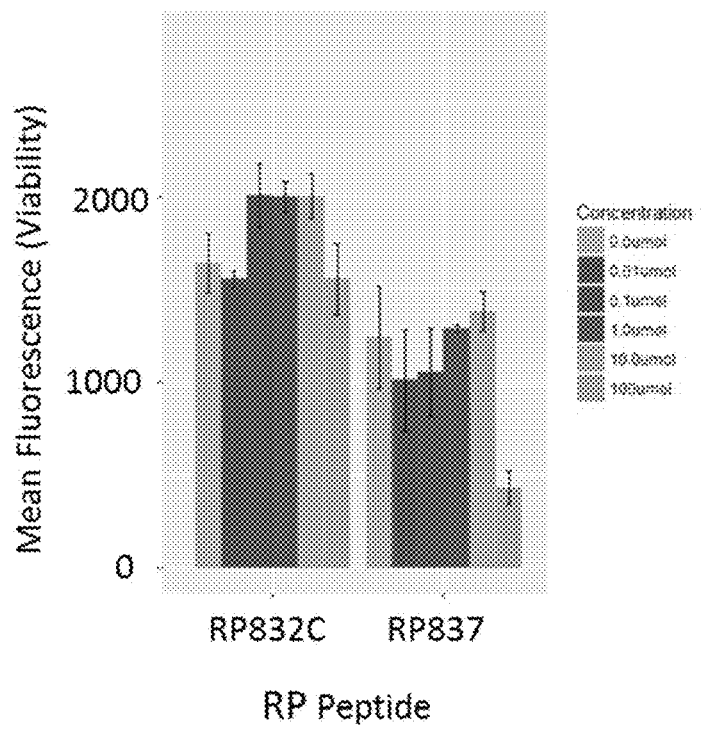
FIG. 4A-4B show the selective effect of exemplary peptides RP832C and RP837 on macrophage samples from scleroderma patients with high arginase:IFNg (interferon-gamma) ratio (FIG. 4B) versus samples from healthy controls with low arginase:IFNg ratio (FIG. 4A).
Figure 4B:
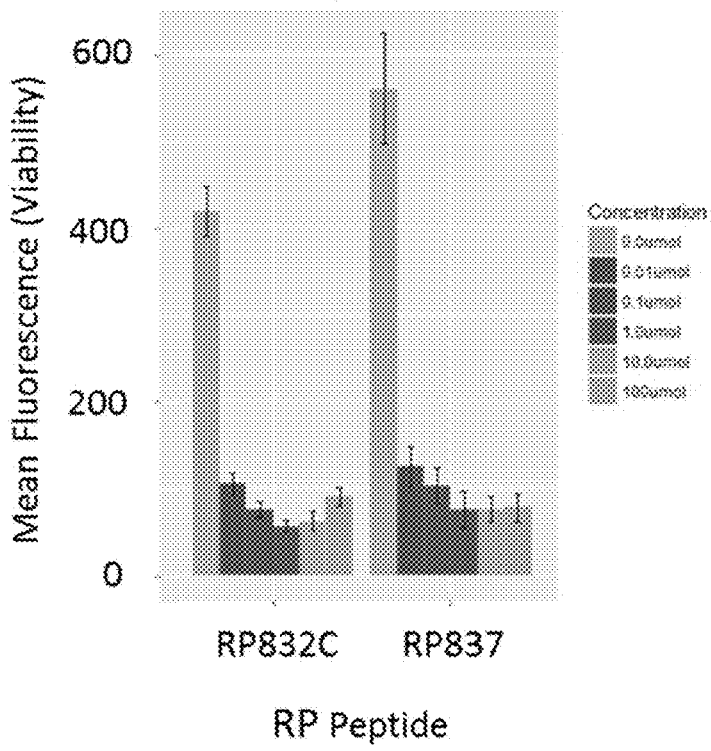

Example 4: Selective Effect of RP Peptides of Interest on Scleroderma Macrophage Viability Peripheral blood derived macrophages were cultured from healthy volunteers and scleroderma patients and cultured in MCS-F for 7 days prior to qPCR for arginase1 (M2 marker) or IFNg (M1 marker), followed by treatment with RP peptides at a range of doses 0-100 uM. After 48 hours media were exchanged and cells were retreated with the peptides. After 96 hours cell viability was assayed by PrestoBlue assay. (FIG. 4A) Macrophages from a healthy control with low arginase:IFNg ratio of 3.6, were resistant to the effects of RP peptides of interest (RP182, RP185, RP832C, RP837) on viability. (FIG. 4B): In a scleroderma (SSc) patient with a raised arginase:IFNg ratio of 8.8, RP peptides of interest (RP182, RP185, RP832C, RP837) even at 0.01 uM greatly reduced viability at 96 hours.

Example 5: Bleomycin Lung Fibrosis Rescue

Intratracheal instillation (IT) of bleomycin was used as a model for lung fibrosis. Rescue of bleomycin-induced lung fibrosis in mice by the subject peptides was studied. Experimental parameters: Four groups (n=8) of C57BL6 male mice were studied over 6-8 weeks. 2.5 U/kg bleomycin was administered IT in a single bolus. After 72 hours, 1 mg/kg peptide of interest (RP182, RP185, RP832, RP837) was administered IT q2D. In this bleomycin challenge experiment, the fibrosis measurements are Ashcroft scores following trichrome staining. Collagen scores are quantitative measurements following hydroxyproline staining. FIG. 1 shows a graph of these results.

The subject peptides reduced fibrosis and collagen deposition. Hematoxylin and eosin (H/E) and Mason's Trichrome staining of lung tissue sections was performed. The alveoli of the vehicle groups appear surrounded by fibrotic tissue with increased collagen deposits unlike the alveoli of the treated and naïve lung groups. Body weight changes: The body weight of RP peptide treatment groups showed no significant change when compared to the body weight of the vehicle treated groups. Ashcroft score analysis: The vehicle group lung specimens showed deformed lung architecture with increased fibrosis and collagen deposition and hence were assigned a score close to 6, unlike the peptide-treated group that showed well organized lung architecture and hence a lower score.

Fibrosis and Collagen deposition level assessment: There was a significant decrease of fibrosis and collagen deposition in the treated group compared to the vehicle group as measured by ImageJ software. Lung weight changes: The vehicle group had higher lung weight compared to the peptide treated group due to decreased fibrosis and collagen contents of the peptide treated group. IHC staining of TGFβ1 and αSMA: Peptide treated lung tissues showed significant decrease in fibrosis associated markers of TGFβ1 and αSMA.

These results demonstrate the exemplary peptides provided a reduction in bleomycin-induced lung fibrosis in a mouse model for lung fibrosis.

Example 6: RP Peptides of Interest Synergize with a PD-1 Checkpoint Inhibitor in CT26 Xenograft FIG. 2 shows the results of a study of the effects of peptides of interest with and without an anti-PD1 antibody on tumor volume in a mouse tumor inhibition model. The peptides RP832C and RP185 were administered at 10 mg/kg qd. The anti-PD1 antibody was administered intraperitoneally at 200 ug twice per week. The results provided in the Examples demonstrate the efficacy of the peptides of the invention.

Nothwithstanding the appended claims, the following clauses are provided to illustrate aspects of the present disclosure.

Clause 1. An immunomodulatory peptide of 5 to 30 (e.g., 6 to 30 or 6 to 18) amino acid residues in length, the peptide comprising: a striapathic region of alternating hydrophilic and hydrophobic modules (e.g., having a length of 6 to 12 or 6 to 10 amino acid residues) described by one of formulae 1-7 that adopts an amphipathic conformation under physiological conditions, comprising: 2 or more (e.g., 3 or more or 4 or more) hydrophobic modules; and one or more (e.g., 2 or more or 3 or more) hydrophilic modules each comprising at least one cationic residue; wherein the immunomodulatory peptide specifically binds CD206.

Clause 2. The immunomodulatory peptide according to clause 1, wherein the striapathic region is of Formula 5 and has a sequence defined by the formula:

$$[J_{1a}J_{1b}]\text{-}[X_{1a}X_{1b}]\text{-}[J_{2a}J_{2b}HX_{2a}X_{2b}HJ_{3a}HX_{3a}] \quad \text{(Formula 5A)};$$

wherein: $J_{1a}$, $J_{1b}$, $J_{2a}$, $J_{2b}$ and $J_{3a}$ are each independently selected from a hydrophobic amino acid residue (e.g., phenylalanine, tryptophan, alanine, valine, and glycine); and $X_{1a}$, $X_{1b}$, $X_{2a}$, $X_{2b}$ and $X_{3a}$ are each independently selected from a hydrophilic amino acid residue (e.g., lysine, arginine, histidine, aspartic acid, glutamic acid, asparagine or glutamine).

Clause 3. The immunomodulatory peptide according to clause 2, wherein: $J_{1a}$, $J_{1b}$, $J_{2a}$, $J_{2b}$ and $J_{3a}$ are each independently selected from phenylalanine, tryptophan, alanine and glycine; and $X_{1a}$, $X_{1b}$, $X_{2a}$, $X_{2b}$ and $X_{3a}$ are each independently selected from lysine and arginine.

Clause 4. The immunomodulatory peptide according to clause 2, wherein: $J_{1a}$, $J_{1b}$, $J_{2a}$, $J_{2b}$ and $J_{3a}$ are each independently selected from phenylalanine, tryptophan, alanine and valine; and $X_{1a}$, $X_{1b}$, $X_{2a}$, $X_{2b}$ and $X_{3a}$ are each independently selected ornithine, lysine and arginine.

Clause 5. The immunomodulatory peptide according to one of clauses 2-4, having the sequence defined by the formula: $FAX_{1a}X_{1b}FAX_{2a}X_{2b}J_{3a}FX_{3a}$ (SEQ ID NO: 30) wherein $X_{1a}$, $X_{1b}$, $X_{2a}$, $X_{2b}$ and $X_{3a}$ are each independently selected from ornithine, lysine and arginine.

Clause 6. The immunomodulatory peptide according to clause 5, having the sequence FAOOFAOOFO (SEQ ID NO:19) (RP850).

Clause 7. The immunomodulatory peptide according to clause 2-4, having the sequence defined by the formula: $FWKX_{1b}FVX_{2a}KWX_{3a}$ (SEQ ID NO: 31) wherein $X_{1b}$, $X_{2a}$ and $X_{3a}$ are each independently lysine or arginine.

Clause 8. The immunomodulatory peptide according to clause 7, having a sequence selected from FWKRFVRKWR (SEQ ID NO:4) (RP837) and FWKKFVKKWK (SEQ ID NO:7) (RP841).

Clause 9. The immunomodulatory peptide according to clause 8, wherein: $J_{1a}$, $J_{1b}$, $J_{2a}$, $J_{2b}$ and $J_{3a}$ are each tryptophan; and $X_{1a}$, $X_{1b}$, $X_{2a}$, $X_{2b}$ and $X_{3a}$ are each independently selected from histidine, lysine and arginine.

Clause 10. The immunomodulatory peptide according to clause 9, having the sequence defined by the formula: $WWX_{1a}HWWHX_{2b}WX_{3a}$ (SEQ ID NO: 32) wherein $X_{1a}$, $X_{2b}$ and $X_{3a}$ are each independently histidine, lysine or arginine.

Clause 11. The immunomodulatory peptide according to clause 10, having a sequence selected from WWHHWWH- HWH (SEQ ID NO:13), WWRHWWHRWR (SEQ ID NO:14), and WWKHWWHKWK (SEQ ID NO:15) (RP 847-849).

Clause 12. The immunomodulatory peptide according to clause 1, wherein the striapathic region is of Formula 6 and has a sequence defined by the formula:

$$[J_{1a}]-[X_{1a}X_{1b}]-[J_{2a}J_{2b}]-[X_{2a}]-[J_{3a}]-[X_{3a}X_{3b}]-[J_{4a}J_{4b}] \quad \text{(formula 6A)};$$

wherein $J_{1a}$, $J_{2a}$, $J_{2b}$, $J_{3a}$, $J_{4a}$ and $J_{4b}$ are each independently selected from a hydrophobic amino acid residue (e.g., phenylalanine, tryptophan, alanine, isoleucine, valine, and glycine); and $X_{1a}$, $X_{1b}$, $X_{2a}$, $X_{3a}$ and $X_{3b}$ are each independently selected from a hydrophilic amino acid residue (e.g., lysine, arginine, histidine, aspartic acid, glutamic acid, asparagine or glutamine).

Clause 13. The immunomodulatory peptide according to clause 12, having the sequence GDRGIKGHRGF (SEQ ID NO:8) (RP842).

Clause 14. The immunomodulatory peptide according to clause 1, wherein the striapathic region is of Formula 1 and has a sequence defined by one of the formulae: $[J_{1a}J_{1b}]$-$[X_{1a}X_{1b}]$-$[J_{2a}J_{2b}]$ (Formula 1A); and $[J_{2b}J_{2a}]$-$[X_{1b}X_{1a}]$-$[J_{1b}J_{1a}]$ (Formula 1B);

wherein: $J_{1a}$, $J_{1b}$, $J_{2a}$ and $J_{2b}$ are each independently selected from a hydrophobic amino acid residue (e.g., phenylalanine, tryptophan and valine); and $X_{1a}$ and $X_{1b}$ are each independently selected from a hydrophilic amino acid residue (e.g., lysine or arginine).

Clause 15. The immunomodulatory peptide according to clause 14, having a sequence FWKRFV (SEQ ID NO:5) (RP837N).

Clause 16. The immunomodulatory peptide according to clause 1, wherein the striapathic region is of Formula 2 and has a sequence defined by the formula:

$$[J_{1a}J_{1b}]-[X_{1a}X_{1b}]-[J_{2a}]-[X_{2a}] \quad \text{(Formula 2A)}$$

wherein: $J_{1a}$, $J_{1b}$, $J_{2a}$ and $J_{2b}$ are each independently selected from a hydrophobic amino acid residue (e.g., phenylalanine, tryptophan and valine); and $X_{1a}$, $X_{1b}$ and $X_{2a}$ are each independently selected from a hydrophilic amino acid residue (e.g., lysine or arginine).

Clause 17. The immunomodulatory peptide according to clause 16, having a sequence FVRKWR (SEQ ID NO:6) (RP837C[1]).

Clause 18. The immunomodulatory peptide according to clause 1, wherein the striapathic region is of Formula 4 and has a sequence defined by one of the formulae: $[J_{1a}J_{1b}]$-$[X_{1a}X_{1b}]$-$[J_{2a}J_{2b}]$-$[X_{2a}X_{2b}]$-$[J_{3a}J_{3b}]$ (Formula 4A); and $[J_{3a}J_{3b}]$-$[X_{2a}X_{2b}]$-$[J_{2b}J_{2a}]$-$[X_{1b}X_{1a}]$-$[J_{1b}J_{1a}]$ (Formula 4B); wherein $J_{1a}$, $J_{1b}$, $J_{2a}$, $J_{2b}$, $J_{3a}$ and $J_{3b}$ are each independently selected from a hydrophobic amino acid residue (e.g., phenylalanine, tyrosine or leucine); and $X_{1a}$, $X_{1b}$, $X_{2a}$ and $X_{2b}$ are each independently selected from a hydrophilic amino acid residue (e.g., lysine or arginine).

Clause 19. The immunomodulatory peptide according to clause 18, having the sequence LYKKIIKKLL (SEQ ID NO:12) (RP846).

Clause 20. The immunomodulatory peptide according to clause 1, wherein the striapathic region is of Formula 4 and has a sequence defined by the formula:

$$[J_{1a}J_{1b}J_{1c}]-[X_{1a}]-[J_{2a}J_{2b}]-[X_{2a}X_{2b}]-[J_{3a}J_{3b}] \quad \text{(Formula 4C)};$$

wherein $J_{1a}$, $J_{1b}$, $J_{1c}$, $J_{2a}$, $J_{2b}$, $J_{3a}$, and $J_{3b}$ are each independently selected from a hydrophobic amino acid residue (e.g., phenylalanine, tyrosine or proline); and $X_{1a}$, $X_{2a}$ and $X_{2b}$ are each independently selected from a hydrophilic amino acid residue (e.g., aspartic acid, lysine or arginine).

Clause 21. The immunomodulatory peptide according to clause 20, having the sequence FYPDFFKKFF (SEQ ID NO:10) (RP844).

Clause 22. The immunomodulatory peptide according to clause 1, wherein the striapathic region is of Formula 4 and has a sequence defined by the formula: $[J_{1a}J_{1b}]$-$[X_{1a}X_{1b}]$-$[J_{2a}]$-$[X_{2a}X_{2b}X_{2c}]$-$[J_{3a}J_{3b}]$ (Formula 4D); wherein $J_{1a}$, $J_{1b}$, $J_{2a}$, $J_{3a}$ and $J_{3b}$ are each independently selected from a hydrophobic amino acid residue (e.g., phenylalanine, serine, glycine or isoleucine); and $X_{1a}$, $X_{1b}$, $X_{2a}$, $X_{2b}$ and $X_{3a}$ are each independently selected from a hydrophilic amino acid residue (e.g., glutamic acid, aspartic acid, lysine or arginine).

Clause 23. The immunomodulatory peptide according to clause 22, having the sequence FFRKSKEKIG (SEQ ID NO:18) (RP853).

Clause 24. The immunomodulatory peptide according to clause 1, wherein the striapathic region is of Formula 4 and has a sequence defined by the formula: $[J_{1a}J_{1b}]$-$[X_{1a}X_{1b}]$-$[J_{2a} J_{2b}]$-$[X_{2a}X_{2b}]$-$[J_{3a}]$ (Formula 4E); wherein $J_{1a}$, $J_{1b}$, $J_{2a}$, $J_{2b}$ and $J_{3a}$ are each independently selected from a hydrophobic amino acid residue (e.g., phenylalanine, alanine or isoleucine); and $X_{1a}$, $X_{1b}$, $X_{2a}$, $X_{2b}$ and $X_{3a}$ are each independently selected from a hydrophilic amino acid residue (e.g., ornithine, lysine or arginine).

Clause 25. The immunomodulatory peptide according to clause 1, wherein the striapathic region is of Formula 5 and has a sequence defined by the formula: $[J_{1a}]$-$[X_{1a}]$-$[J_{2a}J_{2b}J_{1c}]$-$[X_{2a}]$-$[J_{3a}J_{3b}]$-$[X_{3a}X_{3b}]$ (Formula 5C); wherein $J_{1a}$, $J_{2a}$, $J_{2b}$, $J_{2c}$, $J_{3a}$, and $J_{3b}$ are each independently selected from a hydrophobic amino acid residue (e.g., phenylalanine, leucine, glycine or isoleucine); and $X_{1a}$, $X_{2a}$, $X_{3a}$ and $X_{3b}$ are each independently selected from a hydrophilic amino acid residue (e.g., glutamine, lysine or histidine).

Clause 26. The immunomodulatory peptide according to clause 25, having the sequence FQFLGKIIHH (SEQ ID NO: 17) (RP852).

Clause 27. The immunomodulatory peptide according to clause 1, wherein the striapathic region is of Formula 7 and has a sequence defined by the formula: $[X_{1a}X_{1b}]$-$[J_{1a}]$-$[X_{2a}]$-$[J_{2a}]$-$[X_{3a}]$-$[J_{3a}J_{3b}J_{3c}]$ (Formula 7A); wherein $J_{1a}$, $J_{2a}$, $J_{3a}$, $J_{3b}$, and $J_{3c}$ are each independently selected from a hydrophobic amino acid residue (e.g., isoleucine, valine, leucine, serine or alanine); and $X_{1a}$, $X_{1b}$, $X_{2a}$ and $X_{3a}$ are each independently selected from a hydrophilic amino acid residue (e.g., lysine or arginine).

Clause 28. The immunomodulatory peptide according to clause 27, having the sequence KKIRVRLSA (SEQ ID NO: 16) (RP851).

Clause 29. The immunomodulatory peptide according to clause 1, wherein the striapathic region is of Formula 5 and has a sequence defined by the formula: $[J_{1a}J_{1b}]$-$[X_{1a}X_{1b}]$-$[J_{2a}J_{2b}J_{2c}]$-$[X_{2b}]$-$[J_{3a}]$-$[X_{3a}]$ (Formula 5B);

wherein $J_{1a}$, $J_{1b}$, $J_{2a}$, $J_{2b}$ and $J_{3a}$ are each independently selected from a hydrophobic amino acid residue (e.g., phenylalanine, alanine, threonine or leucine); and $X_{1a}$, $X_{1b}$, $X_{2a}$, $X_{2b}$ and $X_{3a}$ are each independently selected from a hydrophilic amino acid residue (e.g., histidine, aspartic acid, lysine or arginine).

Clause 30. The immunomodulatory peptide according to clause 29, having the sequence FFRHFATHLD (SEQ ID NO:11) (RP845).

Clause 31. The immunomodulatory peptide according to clause 40, wherein the striapathic region is of Formula 3 and has a sequence defined by the formula: $[X_{1a}X_{1b}]$-$[J_{1a}J_{1b}J_{1c}J_{1c}J_{1d}]$-$[X_{2a}X_{2b}]$-$[J_{2a'}J_{2b}]$ (Formula 3A); wherein: $J_{1a}$, $J_{1b}$, $J_{1c}$, $J_{1d}$, $J_{2a}$ and $J_{2b}$ are each independently selected from a hydrophobic amino acid residue (e.g., leucine, serine, alanine or phenylalanine); and $X_{1a}$, $X_{1b}$, $X_{2a}$ and $X_{2b}$ are each independently selected from a hydrophilic amino acid residue (e.g., glutamic acid, aspartic acid, lysine, asparagine or arginine).

Clause 32. The immunomodulatory peptide according to clause 31, having a sequence EKLSAFRNFF (SEQ ID NO:9) (RP843).

Clause 33. The immunomodulatory peptide according to clause 1, wherein the striapathic region comprises a dimer of first and second polypeptides connected via a peptide linker that connects the C-terminus of the first polypeptide and the N-terminus of the second polypeptide.

Clause 34. The immunomodulatory peptide according to clause 33, wherein: the hydrophilic modules consist of amino acid residues selected from lysine, arginine and ornithine; and the hydrophobic modules consist of amino acid residues selected from phenylalanine and tryptophan.

Clause 35. The immunomodulatory peptide according to clause 33 or 34, wherein the first and second polypeptides comprise one of the following formulae: [X1]-[J1]-[X2]-[J2] (Formula 3); or [J1]-[X1]-[J2]-[X2] (Formula 2).

Clause 36. The immunomodulatory peptide according to any one of clauses 33-35, wherein the dimer has one of the following formulae: [X1]-[J1]-[X2]-[J2]-T-[J2]-[X2]-[J1]-[X1]; or [J1]-[X1]-[J2]-[X2]-T-[X2]-[J2]-[X1]-[J1]; wherein T is the peptide linker.

Clause 37. The immunomodulatory peptide according to clause 36, wherein the dimer has one of the following formulae: $[X_{1a}]$-$[J_{1a}]$-$[X_{2a}]$-$[J_{2a}]$-T-$[J_{2a}]$-$[X_{2a}]$-$[J_{1a}]$-$[X_{1a}]$ (Formula 12A); or $[J_{1a}]$-$[X_{1a}]$-$[J_{2a}]$-$[X_{2a}]$-T-$[X_{2a}]$-$[J_{2a}]$-$[X_{1a}]$-$[J_{1a}]$ (Formula 13A); wherein T is the peptide linker (e.g., a polyglycine linker).

Clause 38. The immunomodulatory peptide according to clause 37, having a sequence selected from RWKFGGFKWR (SEQ ID NO:1) (RP832C) and FKWRGGRWKF (SEQ ID NO:3) (RP837C).

Clause 39. The immunomodulatory peptide according to clause 33 or 34, wherein the dimer has one of the following formulae: $[X_{1a}X_{1b}]$-$[J_{1a}J_{1b}]$-T-$[J_{1b}J_{1a}]$-$[X_{1b}X_{1a}]$ (Formula 8A); or $[J_{1a}J_{1b}]$-$[X_{1a}X_{1b}]$-T-$[X_{1b}X_{1a}]$-$[J_{1b}J_{1a}]$ (Formula 9A); wherein: T is the peptide linker (e.g., a polyglycine linker); $J_{1a}$ and $J_{1b}$ are each independently selected from a hydrophobic amino acid residue (e.g. tryptophan or phenylalanine); and $X_{1a}$ and $X_{1b}$ are each independently selected from a hydrophilic amino acid residue (e.g., asparagine or arginine).

Clause 40. The immunomodulatory peptide according to clause 49, having the sequence FWKRGGRKWF (SEQ ID NO:4) (peptide 837A).

Clause 41. The immunomodulatory peptide according to any one of clauses 1-40, comprising:
  a) a sequence selected from the peptide sequences of Table 3;
  b) a sequence having at least 75% sequence identity (e.g., at least 80%, at least 85%, at least 90% or at least 95% sequence identity) with the sequence defined in a); or
  c) a sequence having one or two amino acid substitutions relative to the sequence defined in a), wherein the one or two amino acid substitutions are substitutions for amino acids according to Table 2 (e.g., a similar amino acid substitution, a conservative amino acid substitutions or a highly conservative amino acid substitution).

Clause 42. The immunomodulatory peptide according to clauses 1-41, consisting of a sequence selected from any one of the sequences of Table 3 (SEQ ID NOs:1-19).

Clause 43. An immunomodulatory peptide of 6 to 30 amino acid residues in length, comprising:
  a) a peptide sequence selected from SEQ ID NO: (1-19) (e.g., RP832C, 837, 837A, 837C, 837N, 841-842, 843-850 and 853); or
  b) a sequence having one or two amino acid substitutions relative to the sequence defined in a), wherein the one or two amino acid substitutions are substitutions for amino acids according to Table 2 (e.g., a similar amino acid substitution, a conservative amino acid substitutions or a highly conservative amino acid substitution).

Clause 44. The immunomodulatory peptide of clause 43, wherein the one or two amino acid substitutions defined in b) consist of substitution of a cationic amino acid of the sequence with an alternative cationic amino acid residue (e.g., K for O, O for K, K for R, etc).

Clause 45. The immunomodulatory peptide of clause 43, comprising the peptide sequence selected from: RWKFGGFKWR (RP832C) (SEQ ID NO: 1), FKWRGGRWKF (RP837C) (SEQ ID NO: 3) and FWKRGGRKWF (RP837A) (SEQ ID NO: 4).

Clause 46. The immunomodulatory peptide of clause 43, comprising the peptide sequence selected from FWKRFV (RP837N) (SEQ ID NO: 5) and FVRKWR (RP837C') (SEQ ID NO: 6).

Clause 47. The immunomodulatory peptide of clause 43, comprising a peptide sequence selected from FAOOFAOOFO (RP850) (SEQ ID NO: 19), FWKRFVRKWR (RP837) (SEQ ID NO: 4) and FWKKFVKKWK and (RP841) (SEQ ID NO: 7).

Clause 48. The immunomodulatory peptide of clause 43, comprising a peptide sequence selected from WWHHWWHHWH (SEQ ID NO: 13), WWRHWWHRWR (SEQ ID NO: 14) and WWKHWWHKWK (SEQ ID NO: 15) (RP847-849).

Clause 49. The immunomodulatory peptide of clause 43, comprising the peptide sequence GDRGIKGHRGF (RP842) (SEQ ID NO: 8).

Clause 50. The immunomodulatory peptide of clause 43, comprising the peptide sequence LYKKIIKKLL (RP846) (SEQ ID NO: 12).

Clause 51. The immunomodulatory peptide of clause 43, comprising the peptide sequence FYPDFFKKFF (RP844) (SEQ ID NO: 10).

Clause 52. The immunomodulatory peptide of clause 43, comprising the peptide sequence FFRKSKEKIG (RP853) (SEQ ID NO: 18).

Clause 53. The immunomodulatory peptide of clause 43, comprising the peptide sequence FFRHFATHLD (RP845) (SEQ ID NO: 11).

Clause 54. The immunomodulatory peptide of clause 43, comprising the peptide sequence EKLSAFRNFF (RP843) (SEQ ID NO: 9).

Clause 55. An immunomodulatory peptide (e.g., of 12 amino acid residues or less in length), comprising a sequence selected from: RWKFGGFKWR (RP832C) (SEQ ID NO: 1), FKWRGGRWKF (RP837C) (SEQ ID NO: 3) and FWKRGGRKWF (RP837A) (SEQ ID NO: 4).

Clause 56. The immunomodulatory peptide of clause 55, consisting of the sequence: RWKFGGFKWR (RP832C) (SEQ ID NO: 1).

Clause 57. The immunomodulatory peptide of clause 55, consisting of the sequence: FKWRGGRWKF (RP837C) (SEQ ID NO: 3).

Clause 58. The immunomodulatory peptide of clause 55, consisting of the sequence: FWKRGGRKWF (RP837A) (SEQ ID NO: 4).

Clause 59. A pharmaceutical composition, comprising the immunomodulatory peptide of any one of clauses 1-58 and a pharmaceutically acceptable carrier.

Clause 60. The pharmaceutical composition of clause 59, wherein the composition is formulated for oral administration, parenteral administration, administration via inhalation, or topical administration.

Clause 61. The pharmaceutical composition of clause 59 or 60, wherein the composition is formulated for intravenous or subcutaneous administration.

Clause 62. The pharmaceutical composition of clause 59 or 60, wherein the composition is formulated for oral administration and further comprises an enteric coating.

Clause 63. The pharmaceutical composition of clause 59 or 60, wherein the composition is formulated for topical delivery in a form selected from the group consisting of: a gel suspension, a cream, microneedle, and infused into a bandage or topical patch.

Clause 64. A method of modulating macrophage activity, the method comprising: contacting a macrophage with a CD206-binding agent to modulate activity of the macrophage.

Clause 65. The method according to clause 64, wherein the CD206-binding agent binds to a mannose-binding site to modulate binding of signal regulatory protein (SIRP)-mannose to CD206.

Clause 66. The method according to any one of clauses 64-65, wherein the CD206-binding agent binds to CD206 with a binding energy of at least −650 kcal/mol.

Clause 67. The method according to any one of clauses 64-66, wherein the CD206-binding agent directly contacts at least one amino acid residue of CD206 selected from Phe-708, Thr-709, Trp-710, Pro-714, Glu-719, Asn-720, Trp-721, Ala-722, Glu-725, Tyr-729, Glu-733, Asn-747, Asp-748, Ser-1691, Cys-1693, Phe-1694 and Phe-1703.

Clause 68. The method according to any one of clauses 64-67 wherein the macrophage activity that is modulated is macrophage polarization.

Clause 69. The method according to any one of clauses 64-68, wherein viability of the macrophage is reduced.

Clause 70. The method according to any one of clauses 64-69, wherein the macrophage is a M2 macrophage or a tumor associated macrophage (TAM).

Clause 71. The method according to any one of clauses 64-70, wherein the CD206-binding agent inhibits macrophage activity.

Clause 72. The method according to any one of clauses 64-71, wherein the CD206-binding agent is an immunomodulatory peptide.

Clause 73. The method according to any one of clauses 64-71, wherein the macrophage is in vitro.

Clause 74. The method according to any one of clauses 64-71, wherein the macrophage is in vivo.

Clause 75. The method according to any one of clauses 64-74, wherein the CD206-binding agent is an immunomodulatory peptide according to any one of clauses 1-58.

Clause 76. A method of treating a subject for a condition associated with chronic inflammation, the method comprising: administering an effective amount of a CD206-binding agent (e.g., an immunomodulatory peptide according to any one of clauses 1-58) to the subject to treat the subject for the condition associated with chronic inflammation.

Clause 77. The method according to clause 76, wherein the condition associated with chronic inflammation is selected from the group consisting of scleroderma or multiple sclerosis, irritable bowel disease, ulcerative colitis, colitis, Crohn's disease, idiopathic pulmonary fibrosis, scleroderma, asthma, keratitis, arthritis, osteoarthritis, rheumatoid arthritis, auto-immune diseases, a feline or human immunodeficiency virus (FIV or HIV) infection, cancer, age-related inflammation and/or stem cell dysfunction, graft-versus-host disease (GVHD), keloids, obesity, diabetes, diabetic wounds, other chronic wounds, atherosclerosis, Parkinson's disease, Alzheimer's disease, macular degeneration, gout, gastric ulcers, gastritis, mucositis, toxoplasmosis, and chronic viral or microbial infections.

Clause 78. The method according to any one of clauses 76-77, wherein the CD206-binding agent is an immunomodulatory peptide according to any one of clauses 1-58.

Clause 79. The method according to clause 77, wherein the condition is cancer.

Clause 80. The method according to clause 79, further comprising administering an effective amount of an additional agent to the subject.

Clause 81. The method according to clause 80, where the additional agent is a chemotherapeutic agent.

Clause 82. The method according to clause 80, wherein the chemotherapeutic agent is selected from Gemcitabine, Docetaxel, Bleomycin, Erlotinib, Gefitinib, Lapatinib, Imatinib, Dasatinib, Nilotinib, Bosutinib, Crizotinib, Ceritinib, Trametinib, Bevacizumab, Sunitinib, Sorafenib, Trastuzumab, Ado-trastuzumab emtansine, Rituximab, Ipilimumab, Rapamycin, Temsirolimus, Everolimus, Methotrexate, Doxorubicin, Abraxane, Folfirinox, Cisplatin, Carboplatin, 5-fluorouracil, Teysumo, Paclitaxel, Prednisone, Levothyroxine, and Pemetrexed.

Clause 83. The method according to clause 81, wherein the chemotherapeutic agent is abraxane.

Clause 84. The method according to clause 81, wherein the chemotherapeutic agent is Gemcitabine or Docetaxel.

Clause 85. The method according to clause 80, where the additional agent is an immunotherapeutic agent.

Clause 86. The method according to clause 85, wherein the immunotherapeutic agent is an immune checkpoint inhibitor.

Clause 87. The method according to clause 86, wherein the immune checkpoint inhibitor is selected from cytotoxic T-lymphocyte-associated antigen 4 (CTLA-4) inhibitors, programmed death 1 (PD-1) inhibitors and PD-L1 inhibitors.

Clause 88. The method according to clause 87, wherein the immune checkpoint inhibitor is selected from ipilimumab, pembrolizumab and nivolumab.

Clause 89. The method according to clause 76, wherein the condition associated with chronic inflammation is a fibrosis.

Clause 90. The method according to clause 76, wherein the condition associated with chronic inflammation is scleroderma.

Clause 91. The method according to any one of clauses 76-90, wherein the CD206-binding agent is an immunomodulatory peptide according to any one of clauses 1-58.

Clause 92. The method according to clause 91, wherein the CD206-binding agent consists of an immunomodulatory peptide of Table 3.

What is claimed is:

1. A peptide of 12 amino acid residues or less in length, comprising a sequence selected from: RWKFGGFKWR (RP832C) (SEQ ID NO: 1), FKWRGGRWKF (RP837C) (SEQ ID NO: 3) and FWKRGGRKWF (RP837A) (SEQ ID NO: 4).

2. The peptide of claim 1, comprising the sequence: RWKFGGFKWR (RP832C) (SEQ ID NO: 1).

3. The peptide of claim 1, comprising the sequence: FKWRGGRWKF (RP837C) (SEQ ID NO: 3).

4. The peptide of claim 1, comprising the sequence: FWKRGGRKWF (RP837A) (SEQ ID NO: 4).

5. The peptide of claim 2, consisting of the sequence: RWKFGGFKWR (RP832C) (SEQ ID NO: 1).

6. The peptide of claim 3, consisting of the sequence: FKWRGGRWKF (RP837C) (SEQ ID NO: 3).

7. The peptide of claim 4, consisting of the sequence: FWKRGGRKWF (RP837A) (SEQ ID NO: 4).

8. A pharmaceutical composition, comprising the immunomodulatory peptide of claim 1 and a pharmaceutically acceptable carrier.

9. The pharmaceutical composition of claim 8, wherein the composition is formulated for oral administration, parenteral administration, administration via inhalation, or topical administration.

10. The pharmaceutical composition of claim 8, wherein the composition is formulated for intravenous or subcutaneous administration.

11. The pharmaceutical composition of claim 8, wherein the composition is formulated for intratumoral administration.

12. The pharmaceutical composition of claim 8, wherein the composition is formulated for oral administration and further comprises an enteric coating.

13. The pharmaceutical composition of claim 8, wherein the composition is formulated for topical delivery in a form selected from: gel suspension, cream, microneedle and infused into a bandage or topical patch.

14. The pharmaceutical composition of claim 8, wherein the immunomodulatory peptide comprises the sequence: RWKFGGFKWR (RP832C) (SEQ ID NO: 1).

15. The pharmaceutical composition of claim 13, wherein the immunomodulatory peptide consists of the sequence: RWKFGGFKWR (RP832C) (SEQ ID NO: 1).

16. The pharmaceutical composition of claim 8, wherein the immunomodulatory peptide comprises the sequence: FKWRGGRWKF (RP837C) (SEQ ID NO: 3).

17. The pharmaceutical composition of claim 16, wherein the immunomodulatory peptide consists of the sequence: FKWRGGRWKF (RP837C) (SEQ ID NO: 3).

18. The pharmaceutical composition of claim 8, wherein the immunomodulatory peptide comprises the sequence: FWKRGGRKWF (RP837A) (SEQ ID NO: 4).

19. The pharmaceutical composition of claim 18, wherein the immunomodulatory peptide consists of the sequence: FWKRGGRKWF (RP837A) (SEQ ID NO: 4).

* * * * *